US011903732B2

(12) United States Patent
Carlile et al.

(10) Patent No.: US 11,903,732 B2
(45) Date of Patent: Feb. 20, 2024

(54) PRENATAL MONITORING DEVICE

(71) Applicant: Owlet Baby Care, Inc., Lehi, UT (US)

(72) Inventors: Ali Carlile, Vineyard, UT (US); Seth Munger, Springville, UT (US); Michael Bunn, Lehi, UT (US)

(73) Assignee: Owlet Baby Care, Inc., Lehi, UT (US)

( * ) Notice: Subject to any disclaimer, the term of this patent is extended or adjusted under 35 U.S.C. 154(b) by 642 days.

(21) Appl. No.: 16/884,184

(22) Filed: May 27, 2020

(65) Prior Publication Data

US 2020/0375537 A1 Dec. 3, 2020

Related U.S. Application Data

(60) Provisional application No. 62/933,573, filed on Nov. 11, 2019, provisional application No. 62/855,033, filed on May 31, 2019.

(51) Int. Cl.
*B29C 65/00* (2006.01)
*A61B 5/00* (2006.01)
(Continued)

(52) U.S. Cl.
CPC .......... *A61B 5/6804* (2013.01); *A61B 5/0011* (2013.01); *A61B 5/053* (2013.01); *B32B 37/12* (2013.01); *B32B 38/0004* (2013.01); *A61B 2562/02* (2013.01); *A61B 2562/14* (2013.01); *A61B 2562/164* (2013.01);
(Continued)

(58) Field of Classification Search
CPC ................................ B32B 37/12; B29C 65/48
See application file for complete search history.

(56) References Cited

U.S. PATENT DOCUMENTS 3,045,678 A 7/1962 Geimer
3,080,869 A 3/1963 Alberts
(Continued)

FOREIGN PATENT DOCUMENTS

CN 105455800 4/2016
CN 205697786 U 11/2016
(Continued)

OTHER PUBLICATIONS

Azimi et al.; "Personalized Maternal Sleep Quality Assessment: An Objective IoT-based Longitudinal Study;" IEEE Access; (2019); pp. 93433-93447; vol. 7; <doi: 10.1109/ACCESS.2019.2927781 >.
(Continued)

*Primary Examiner* — Philip C Tucker
*Assistant Examiner* — Nickolas R Harm
(74) *Attorney, Agent, or Firm* — Workman Nydegger

(57) ABSTRACT

A garment shaped to approximate the abdomen of an expectant mother having a layered laminated conductive material adhered to the garment is disclosed. A portion of the laminated material is configured to directly contact the skin of the maternal abdomen to create an electrical signal connection. A portion of the layered laminated material comprises a stretchable circuit assembly having a substrate with an adhesive layer, a thermoplastic layer, a conductive layer and an encapsulating layer. A monitor controller is disposed about the garment and is configured to receive electrical signals from the circuit assembly and transmit information related to the electrical signals to a remote location.

9 Claims, 28 Drawing Sheets

(51) Int. Cl.
  *A61B 5/053*  (2021.01)
  *B32B 37/12*  (2006.01)
  *B32B 38/00*  (2006.01)
  B29C 65/48  (2006.01)

(52) U.S. Cl.
  CPC ....... *B29C 65/48* (2013.01); *B32B 2037/1215* (2013.01); *B32B 2305/18* (2013.01); *B32B 2307/202* (2013.01); *B32B 2307/51* (2013.01); *B32B 2535/00* (2013.01)

(56) References Cited

U.S. PATENT DOCUMENTS

| | | |
|---|---|---|
| 4,781,200 A | 11/1988 | Baker |
| 5,255,393 A | 10/1993 | Brady |
| 5,571,039 A | 11/1996 | Ford |
| 5,807,271 A | 9/1998 | Tayebi et al. |
| 6,047,203 A | 4/2000 | Sackner et al. |
| 7,333,850 B2 | 2/2008 | Marossero et al. |
| 7,949,389 B2 | 5/2011 | Wolfberg et al. |
| 8,116,855 B2 | 2/2012 | James et al. |
| 8,229,550 B2 | 7/2012 | James et al. |
| 8,275,451 B2 | 9/2012 | Marossero et al. |
| 8,548,558 B2 | 10/2013 | Dunagan et al. |
| 8,747,186 B2 | 6/2014 | Fong |
| 8,798,708 B2 | 8/2014 | Tremblay |
| 8,818,478 B2 | 8/2014 | Scheffler et al. |
| 8,880,140 B2 | 11/2014 | Hayes-Gill et al. |
| 8,892,181 B2 | 11/2014 | Wolfberg et al. |
| 8,897,862 B2 | 11/2014 | Kobayashi et al. |
| 9,456,637 B2 | 10/2016 | Fligel |
| 9,591,983 B2 | 3/2017 | Amir et al. |
| 9,662,030 B2 | 5/2017 | Thng et al. |
| 9,730,476 B1 | 8/2017 | Mahar |
| 9,763,621 B1 | 9/2017 | Hafezi |
| 9,895,105 B2 | 2/2018 | Romem |
| 9,968,291 B2 | 5/2018 | Haves-Gill et al. |
| 10,039,459 B2 | 8/2018 | Oz et al. |
| 10,080,389 B2 | 9/2018 | Melarti et al. |
| 10,105,097 B2 | 10/2018 | Markel |
| 10,154,791 B2 | 12/2018 | Longinotti-Buitoni |
| 10,178,965 B2 | 1/2019 | Howell et al. |
| 10,265,010 B2 | 4/2019 | Larson |
| 10,898,097 B2 | 1/2021 | Hayes-Gill et al. |
| 11,089,992 B2 | 8/2021 | Hayes-Gill et al. |
| 2004/0145089 A1 | 7/2004 | Burrows |
| 2010/0204560 A1 | 8/2010 | Salaheih et al. |
| 2013/0102856 A1 | 4/2013 | Wolfberg |
| 2013/0144365 A1 | 6/2013 | Kipke et al. |
| 2014/0307423 A1 | 10/2014 | Coats |
| 2016/0000374 A1 | 1/2016 | Dandekar et al. |
| 2016/0076175 A1 | 3/2016 | Rock et al. |
| 2016/0128594 A1 | 5/2016 | Amir et al. |
| 2016/0256132 A1 | 9/2016 | Van De Laar et al. |
| 2016/0292584 A1 | 10/2016 | Weinberg et al. |
| 2016/0331299 A1 | 11/2016 | Cline et al. |
| 2017/0036066 A1 | 2/2017 | Chahine |
| 2017/0172426 A1* | 6/2017 | Oz .................. A61B 5/7225 |
| 2017/0281087 A1 | 10/2017 | Workman et al. |
| 2018/0007977 A1 | 1/2018 | Windenberger |
| 2018/0078178 A1 | 3/2018 | Caden et al. |
| 2018/0317783 A1 | 11/2018 | Petrilovsky et al. |
| 2018/0344171 A1 | 12/2018 | Straka et al. |
| 2018/0345015 A1 | 12/2018 | Straka et al. |
| 2019/0000384 A1 | 1/2019 | Gupta et al. |
| 2019/0313830 A1 | 10/2019 | Little et al. |
| 2021/0205113 A1 | 7/2021 | Wong |

FOREIGN PATENT DOCUMENTS

| | | |
|---|---|---|
| CN | 108670518 A | 10/2018 |
| ES | 1188683 U | 6/2017 |
| IN | 201643042957 | 6/2018 |
| JP | 2016/537068 A | 12/2016 |
| WO | WO 2016110804 A1 | 7/2016 |
| WO | WO 2016176632 A1 | 11/2016 |
| WO | WO 2018/161152 A1 | 9/2018 |
| WO | WO 2019/006536 A1 | 1/2019 |
| WO | WO 2019/134031 A2 | 7/2019 |
| WO | WO 2019/134032 A9 | 7/2019 |
| WO | WO 2019/134033 A2 | 7/2019 |
| WO | WO 2019/140704 A1 | 7/2019 |

OTHER PUBLICATIONS

AZMED.; "AZMED Material Belt, Breathable Abdominal Binder, Back Support, One Size, Bridge." Webpage first available Aug. 22, 2015; https://www.amazon.com/AZMED-Maternity-Breathable-Abdominal-Support/dp/B0113WE0QS.

Blanqi.; "Blanqi Everyday Maternity Built-in Support BellyBand." Webpage first accessed on Oct. 3, 2019; https://www.blanqi.com/products/blanqi-maternity-support-bellyband?variant=1114741357.

Roham et al.; "A mobile wearable wireless fetal heart monitoring system."

European Search Report received for EP Patent Application No. 20814817.1, dated Jun. 6, 2023, 5 pages.

International Preliminary Report on Patentability received for PCT Patent Application No. PCT/US20/34618, dated Dec. 9, 2021, 09 pages.

International Search Report and Written Opinion received for PCT Patent Application No. PCT/US20/34618, dated Sep. 11, 2020, 13 pages.

* cited by examiner

PRENATAL MONITORING DEVICE

PRIORITY CLAIM

This application claims priority to Application Ser. No. 62/855,033 filed on May 31, 2019 entitled PRENATAL MONITORING DEVICE and Application Ser. No. 62/933,573 filed on Nov. 11, 2019 entitled PRENATAL MONITORING DEVICE. Both of the foregoing applications are incorporated herein by reference in their entireties.

FIELD OF THE DISCLOSURE

Disclosure embodiments relate generally to medical devices, and more particularly to a close-fitting wearable garment for monitoring prenatal data.

BACKGROUND

Every year, within the United States, a number of pregnancies end with a stillborn child. The causes of many of these stillbirths are unknown. While various risk factors have been identified with stillbirths, many times the actual cause of the stillbirth is not known unless an autopsy, or some other investigative procedure, is performed on the stillborn child. To combat stillbirths and to identify potential problems early in a pregnancy, frequent maternity visits with a doctor are suggested. These visits often involve taking health measurements of both the mother and the unborn child. Through monitoring these health measurements (i.e., "vital signs"), a trained medical professional can track the health of both the baby and the mother, and potentially identify developing problems before they become irreversible. Unfortunately, even with the wide availability of advanced medical care and associated maternity care, many stillbirths continue to occur. As such, there are many problems within the field that remain unsolved.

SUMMARY

Aspects of the technology are directed towards stretchable fabric that extends around an expectant mother's abdomen to accommodate the variety of expectant female shapes. In some aspects, the device uses technology for acquiring maternal and baby heart rate as well as other important vital markers. One aspect comprises a stretchable layered conductive material adhered to the fabric. A portion of the stretchable layered conductive material directly contacts the skin of the maternal abdomen to create an electrical signal connection. In one aspect, the device is configured to comfortably accommodate the different and changing maternal body shape while optimizing contact between the conductive material and the maternal belly and limiting stretch of the device in order to prevent the conductive material from over-stretching to the point of mechanical failure.

BRIEF DESCRIPTION OF THE DRAWINGS

Invention embodiments will become more fully apparent from the following description and appended claims, taken in conjunction with the accompanying drawings. It is to be understood that these drawings merely depict exemplary invention embodiments and are not to be considered limiting of the disclosure's scope. It will be readily appreciated that the components of the embodiments, as generally described and illustrated in the figures herein, could be arranged and designed in a wide variety of different configurations. Nonetheless, the technology will be described and explained with additional specificity and detail through the use of the accompanying drawings in which:

DESCRIPTION OF ASPECTS OF THE TECHNOLOGY

Figure 1:
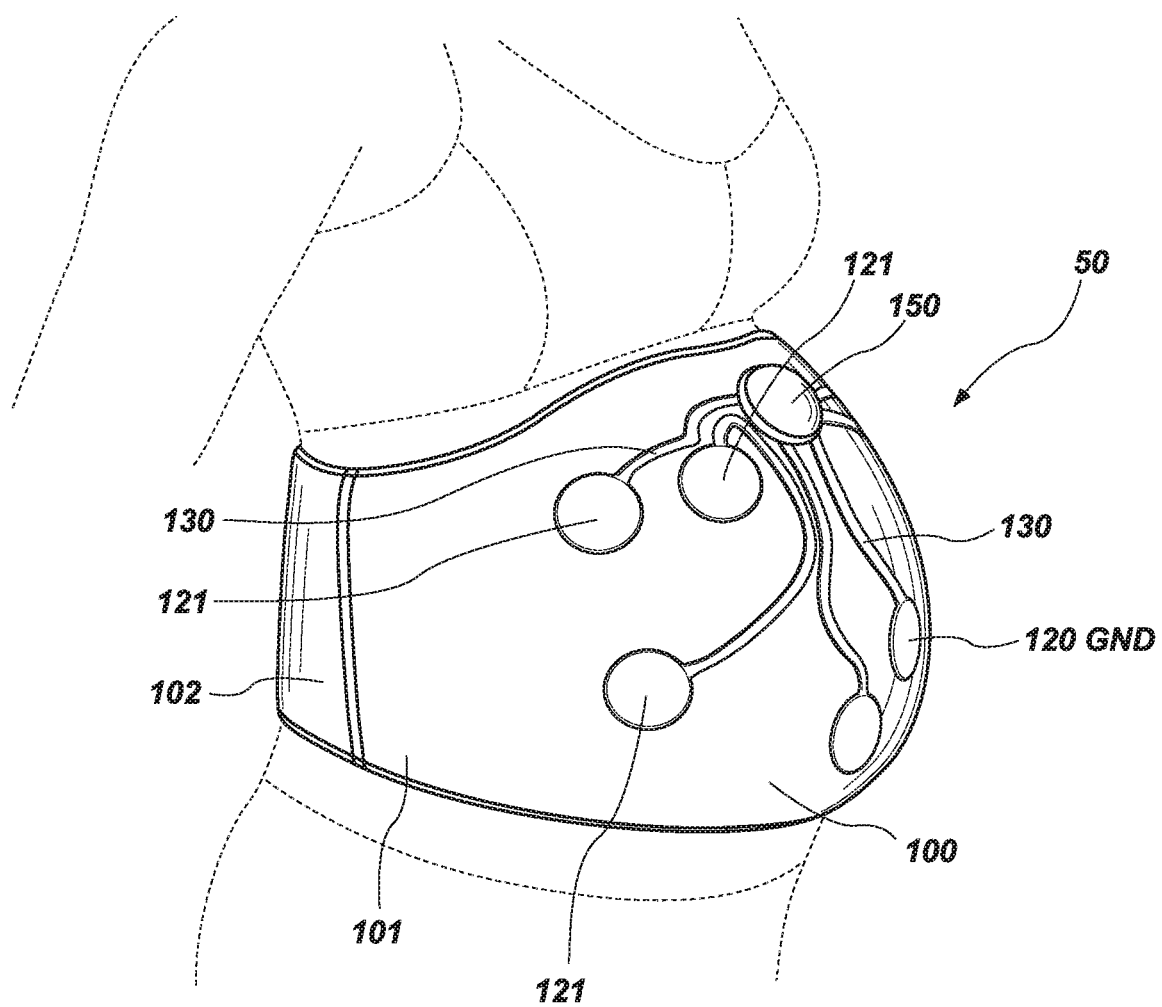
FIG. 1 is a perspective view of a wearable prenatal monitor in accordance with one aspect of the technology.

The following detailed description includes reference to the accompanying drawings, which form a part hereof and in which are shown, by way of illustration, exemplary embodiments. It is believed that the construction of wearable prenatal monitors will improve the performance of the monitor. However, before the present technology is disclosed and described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

Although the following detailed description contains many specifics for the purpose of illustration, a person of ordinary skill in the art will appreciate that many variations and alterations to the following details can be made and are considered to be included herein. Accordingly, the following embodiments are set forth without any loss of generality to, and without imposing limitations upon, any claims set forth. Unless defined otherwise, all technical and scientific terms used herein have the same meaning as commonly understood by one of ordinary skill in the art to which this disclosure belongs.

As used in this specification and the appended claims, the singular forms "a," "an" and "the" include plural referents unless the context clearly dictates otherwise. Thus, for example, reference to "a line" includes a plurality of such lines.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in this specification it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein.

The term "coupled," as used herein, is defined as directly or indirectly connected in a fluidic or non-fluidic manner.

Objects described herein as being "adjacent to" each other may be in physical contact with each other, in close proximity to each other, or in the same general region or area as each other, as appropriate for the context in which the phrase is used.

Occurrences of the phrase "in one embodiment," or "in one aspect," herein do not necessarily all refer to the same embodiment or aspect.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms."

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.8, 3, 3.1, 4, 4.6, and 5, individually.

This same principle applies to ranges reciting only one numerical value as a minimum or a maximum. Furthermore, such an interpretation should apply regardless of the breadth of the range or the characteristics being described.

As used herein, "enhanced," "improved," "performance-enhanced," "upgraded," "improvement," and the like, when used in connection with the description of a device, component, or process, refers to a characteristic of the device, component or process that provides measurably better form, function, or outcome as compared to previously known devices or processes. This applies both to the form and function of individual components in a device or process, as well as to such devices or processes as a whole.

Reference throughout this specification to "an example" means that a particular feature, structure, or characteristic described in connection with the example is included in at least one embodiment. Thus, appearances of the phrase "in an example" in various places throughout this specification are not necessarily all referring to the same embodiment.

The term "biocompatible material" refers to any material with the ability to act and perform without impairing basic immunological functions of the body. Typical biocompatible plastics, for example, include polyvinylchloride or PVC, polyether sulfone or PES, polytetrafluoroethylene or PTFE, polyethylene (PE-UHMW or PE-LD & HD), polyurethane or PU and the like.

The term "stretchability" or "stretchable" as used herein refers to the elastic property of the material and its ability to be stretched without suffering plastic deformation.

Example Embodiments

It should be understood that the aspects of the technology discussed herein are contemplated for use with a wearable maternal monitor. For purposes of illustrating the various aspects of the methods and systems claimed herein, the discussion below will be primarily directed to describing exemplary embodiments directed to a close-fitting garment worn by a pregnant female. It should be noted, however, that the elements and principles discussed herein are applicable to other applications. It is also noted that discussion of methods and systems herein can be interchangeable with respect to specific aspects. In other words, specific discussion of one apparatus, method, or system (or components thereof) herein is equally applicable to other aspects as they relate to the apparatus, system, or method, and vice versa.

An initial overview of technology embodiments is provided below and specific technology embodiments are then described in further detail. This initial summary is intended to aid readers in understanding the technology more quickly, but is not intended to identify key or essential technological features, nor is it intended to limit the scope of the claimed subject matter. In particular, aspects of the technology are directed towards stretchable fabric that extends around an expectant mother's abdomen covering them, in the front, from rib to pubic bone and tapering in the back to accommodate the variety of expectant female shapes. In some aspects of the technology, the device uses Electrical Cardio Gram (ECG) technology for acquiring maternal and baby heart rate as well as other important vital markers. One aspect of the device or garment comprises a layered laminated conductive material adhered to the fabric on the front panel. The laminated material directly contacts the skin of the maternal abdomen to create an electrical signal connection. Because of the great change occurring in a growing maternal body, it is important that the conductive material be placed comfortably against the skin of the maternal abdomen. The conductive material as it is located within the device must be able to bend and stretch to accommodate the variety of maternal body shapes. The conductive material must adhere to the fabric and the covering must block cross connected signals caused by moisture or humidity from perspiration or other sources.

Other aspects of the technology are directed towards stretchable fabric that extends around an expectant mother's abdomen covering them, in the front, from rib to pubic bone and tapering in the back to accommodate the variety of expectant female shapes. In some aspects of the technology, the device uses sensors disposed in contact with the maternal abdomen for acquiring maternal and baby heart rate as well as other important vital markers. One aspect of the device or garment comprises a layered conductive material adhered or otherwise coupled to the fabric on a front panel. The conductive material directly contacts the skin of the maternal abdomen to create an electrical signal connection and allows for contact with the skin without being semi-permanent or embedded into the top layer of skin. Because of the great change occurring in a growing maternal body, it is important that the conductive material be placed comfortably against the skin of the maternal abdomen and remain in place while worn by the expectant mother. The conductive material, as it is disposed about the device, must be able to bend and stretch to accommodate the variety of changing maternal body shapes. In one aspect, the device is configured to comfortably accommodate the different and changing maternal body shape while optimizing contact between the conductive material and the maternal belly and limiting stretch of the device in order to prevent the conductive material from over-stretching to the point of mechanical failure.

Referring generally to FIG. 1, a wearable prenatal monitoring device 50 is disclosed. The device 50 is intended to be worn from approximately 24 weeks of pregnancy until full term, or as directed by a medical practitioner. Fabric is cut to a pattern and assembled into a garment 100 that is configured to closely fit the contours of an expectant mother and to be configurable with her changing contours throughout the course of the pregnancy. In one aspect of the technology, the fabric of the garment 100 may be a stretchable fabric, for example a woven elastomer in the class of segmented co-polyesters such as polyester-polyurethane copolymer fibers alone or blended with cotton or other natural fibers or synthetic polymer fibers such as polyester, nylon, acrylic, and the like. For example, in one aspect of the technology, the fabric of the garment comprises a nylon, polyester, spandex blend. In one aspect, the fabric comprises approximately 91.5% nylon and approximately 8.5% spandex. The fabric is configured to wrap around the body of the mother and couple to itself using hook and loop fasteners, snaps, zippers, belts, or other fasteners known in the art. In one aspect of the technology, a hook and loop fastener is used wherein the distal end of the hook is cushioned by a wide loop pad. That is, the base of the loop is wider than the hook which minimizes the likelihood that the hook will contact the underlying fabric.

With reference generally to FIGS. 1 and 19-21, in one aspect of the technology, the garment 100 comprises one or more separate pieces configured to be coupled together when worn by the user. In one aspect, the garment 100 comprises a front piece or front panel 1110 that carries the electronics, sensors, and related materials used to monitor prenatal data. The garment 100 further comprises a back piece or back panel 1200 that couples to the front piece 1110 and is intended to provide a support mechanism for holding the front piece 1110 firmly against the abdomen of the user. While two pieces are referenced herein, it is understood that the garment 100 may comprise a single integrated piece of fabric or multiple pieces of fabric as suits a particular application.

With reference generally to FIG. 1, the garment 100 is provided with a plurality of electrodes 120 integrated or coupled to the fabric. Namely, a ground electrode 120 GND and a plurality of abdominal electrodes 121 are disposed about the garment 100 in the area that is configured to fit about the abdomen of the expectant mother. The ground electrode 120 GND may be located anywhere on the body. A monitor controller 150 is electrically coupled to the electrodes by way of a plurality of conductive pathways 130. The monitor controller 150 receives the signals from the conductive pathways 130. These conductive pathways 130 may be embodied in the form of conductive wires incorporated into the garment fabric. Generally speaking, the non-ground electrodes are intended to measure the contractions of the expectant mother and the heartbeat of her baby. The electrodes near the top of the abdomen are generally responsible for the detection of contractions while the electrodes near the bottom of the abdomen are responsible for detection of the heartbeat of the baby. Other data, of course, is gathered regarding the health of the mother and the baby, including the maternal heart rate, the general sleep position of the mother (e.g., sleeping on front, back, or side, etc.), and general movement of the baby (e.g., kicking, breathing or movement of the fetal diaphragm, hiccups, etc.).

While general reference is made to the primary responsibility of certain of the electrodes in terms of their data gathering function, it is understood that all of the electrodes work in tandem to gather useable information. In certain aspects of the technology, the comparison of different data points collected over time by the different electrodes is used to provide useful information to the expectant mother and/or her medical care provider or other interested persons. Moreover, other sensors can be used and incorporated into the garment 100 or monitor controller 150 to gather additional information, including pulse oximeters, accelerometers, and the like.

Broadly speaking, in one aspect of the technology, the garment 100 comprises a stretchable integrated electrode/circuit assembly 200. The electrode assembly is pre-assembled in a format configured to be adhered to the garment 100 to form the monitoring device 50. In one aspect, the integrated electrode assembly 200 comprises a base film 210 coupled to a conductive material 220. A sensor (i.e., the electrodes) is disposed about a portion of the conductive material and is disposed within an encapsulant. A cover film is disposed atop the encapsulant 245. In one aspect of the technology, the materials that are deposited on the base film (conductive layer 220, encapsulant 245, etc.) are printed onto the base film 210 with a screen printer as is known in the art. While not required at every step, in one aspect of the technology, after each layer is printed or deposited on the base film 210, the film is sent through a curing or drying tunnel before the next layer is printed thereon.

In one aspect of the technology, the base film or substrate 210 comprises a polymer thick film composition for use in electrical circuits and, in particular, highly stretchable deformed circuits such as those applications where functional circuitry is generated on fabrics for clothing. Conductive material or a conductive subassembly 220 is printed and dried on a substrate or base film 210 so as to produce a functioning circuit wherein the entire circuit is subjected to the typical bending/creasing that a fabric would experience about the abdomen of an expectant mother. Because the circuitry is subjected to washing and drying on a periodic basis, as is customary with garments, the conductive material 220 must maintain conductive integrity. In one aspect of the technology, the base film 210 can be Dupont® Intexar™ TE-11C or another stretchable polymeric film. Generally speaking, the base film 210 comprises a high recovery thermoplastic layer and a melt adhesive layer. The melt adhesive layer is covered by a carrier film. Melt adhesives include ethylene-vinyl acetates, polyolefins, polyamides, polyurethanes, polyesters, and the like. In one aspect of the technology, an additional melt adhesive layer such as Bemis™ Hotmelt 3415 C can be used. Once a functioning circuit has been created on the high recovery side of the base film 210, the carrier film is removed and circuit is bonded to the fabric of the garment 100 under heat press lamination. In one aspect of the technology, after printing of the circuit on the base film 210 is complete and the circuit is cut to a desired pattern, the circuit is placed in contact with the fabric in a clamshell press under substantially uniform temperature and pressure. In one aspect of the technology, the temperature is set at between 125 and 140° C. under a pressure ranging from 0.5 to 0.7 MPa gauge pressure for a dwell time ranging from between 15 and 40 seconds. In another aspect, the temperature is set at 135° C. at a pressure from 0.6 MPa for a dwell time of 35 seconds.

In one aspect of the technology, thermoplastic substrates, including thermoplastic polyurethane substrates (TPU's), along with the series of polymer thick film (PTF) compositions are used to produce stretchable circuits that can be used in making wearable electronics in washable garments. While TPU compositions are specifically referenced, the substrate may include polyester (PET), polycarbonate, and similar compositions. In some aspects of the technology, the electrically conductive material or PTF (sometimes referred to as a conductive "ink" or "PTF ink") comprises (i) silver flakes, or silver flakes and silver chloride powder or graphite, conductive carbon or mixtures thereof and (ii) an organic medium comprising a polymer resin dissolved in an organic solvent. When the electrically conductive metal powder is replaced by fumed silica, the PTF composition or ink serves as an encapsulant. Additionally, other powders and printing aids may be added to improve the composition.

Conductor Compositions

In one aspect of the technology, the electrically conductive metal used to form the PTF ink is selected from the group consisting of Ag, Cu, Au, Pd, Pt, Sn, Al, Ni, an alloy of Ag, Cu, Au, Pd, Pt, Sn, Al, Ni and mixtures thereof. In one aspect, the conductive metals include silver (Ag), Carbon (C), or a carbon composite. In a further aspect, the conductive metals may, for example, include one or more of the following: Ag, Cu, Au, Pd, Pt, Sn, Al, Ni, Ag—Pd and Pt—Au. In another aspect, the conductive metals include one or more of the following: (1) Al, Cu, Au, Ag, Pd and Pt; (2) an alloy of Al, Cu, Au, Ag, Pd and Pt; and (3) mixtures thereof. In still another aspect, the conductive metals include one of the above-mentioned metals coated with another of the metals, e.g., Ag-coated Cu, Ag-coated-Ni. One aspect of the technology, contains a mixture of any of the above in powdered or particle form or in a liquid, gel, or other form that is suitable for placement on a stretchable substrate.

In one such aspect, the electrically conductive metals are silver powders and may comprise silver metal powder, alloys of silver metal powder, or mixtures thereof. Various particle diameters and shapes of the conductive powder are contemplated. In an embodiment, the conductive powder may include any shape silver powder, including spherical particles, flakes (rods, cones, plates), and mixtures thereof. In one embodiment, the conductive powder is in the form of silver flakes. In an aspect of the technology, the particle size distribution of the conductive powders may be 1 to 100 microns; in a further embodiment, 2-10 microns. In one aspect, the surface area/weight ratio of the silver particles may be in the range of 0.1-1.0 m2/g. Furthermore, small amounts of other metals may be added to silver conductor compositions to improve the properties of the conductor. Some examples of such metals include: gold, copper, nickel, aluminum, platinum, palladium, molybdenum, tungsten, tantalum, tin, indium, lanthanum, gadolinium, boron, ruthenium, cobalt, titanium, yttrium, europium, gallium, sulfur, zinc, silicon, magnesium, barium, cerium, strontium, lead, antimony, conductive carbon, and combinations thereof and others common in the art of thick film compositions. The additional metal(s) may comprise up to about 1.0 percent by weight of the total composition. In various embodiments, the electrically conductive metal powder may be present at 20 to 92 wt %, 30 to 70 wt %, or 45 to 65 wt % based on the total weight of the composition. In another conductor aspect, the functional component is silver powder in combination with silver chloride powder. This combination is present at 20 to 92 wt %, based on the total weight of the composition. The ratio of the weight of the silver powder to the weight of the silver chloride powder is in the range of 9 to 1 to 0.1 to 1. In one aspect, the silver powder is in the form of silver flakes. The functional powder may consist of graphite, conductive carbon or mixtures and the resulting composition can be used as a protective ink to form an overcoat. The amount of graphite, conductive carbon or mixtures may be present at 20 to 92 wt %, based on the total weight of the composition.

Organic Medium

In one aspect of the technology, the organic medium is comprised of a thermoplastic polyurethane resin dissolved in an organic solvent. The polyurethane resin must achieve good adhesion to an underlying substrate. The polyurethane resin is compatible with and does not adversely affect the performance of the circuit after deformation and wash and dry cycles.

In one aspect, the thermoplastic polyurethane resin is 5-50 wt % of the total weight of the organic medium. In another aspect, the thermoplastic polyurethane resin is 20-45 wt % of the total weight of the organic medium and in still another embodiment the thermoplastic polyurethane resin is 23-30 wt % of the total weight of the organic medium. In another aspect, the thermoplastic polyurethane resin is a polyurethane homopolymer. In another aspect, the polyurethane resin is a polyester-based copolymer. In one aspect, the thermoplastic polyurethane resin is a predominantly linear hydroxyl polyurethane. The thermoplastic polyurethane resin also has a tensile stress necessary to achieve 100% elongation of less than 1000 pounds per square inch (psi).

The polymer resin is typically added to the organic solvent by mechanical mixing to form the medium. Solvents suitable for use in the polymer thick film composition include acetates and terpenes such as carbitol acetate and alpha- or beta-terpineol or mixtures thereof with other solvents such as kerosene, dibutylphthalate, butyl carbitol, butyl carbitol acetate, hexylene glycol and high boiling alcohols and alcohol esters. In addition, volatile liquids for promoting rapid hardening after application on the substrate may be included. In many embodiments of the present invention, solvents such as glycol ethers, ketones, esters and other solvents of like boiling points (in the range of 180° C. to 250° C.), and mixtures thereof may be used. Various combinations of these and other solvents are formulated to obtain the viscosity and volatility requirements desired. Solvent may be added to the composition to adjust the viscosity and may be considered part of the organic medium. In various aspects, the organic medium may be present at 8 to 80 wt %, 30 to 70 wt %, or 35 to 55 wt % based on the total weight of the composition.

In accordance with one aspect of the technology, the compositions may be formulated to be used as an overcoat to protect the conductor formed from the polymer thick film conductor compositions discussed above from environmental degradation. A polymer thick film overcoat composition is formulated by using graphite, conductive carbon or a mixture thereof and the organic medium mentioned above. The overcoat results in a minimal shift in resistance of the conductor.

Encapsulant Composition

In one aspect of the technology, the encapsulant is directly deposited onto the conductor or is applied over an overcoat layer. The composition is formulated by using an organic medium with the addition of fumed silica as a powder and/or the addition of a dye as needed. The amount of fumed silica used is from 0.1 to 3 wt % and the amount of organic medium is from 97 to 99.9 wt %, based on the total weight of the composition. In one embodiment, the amount of fumed silica used is from 0.5 to 1.5 wt % and the amount of organic medium is from 98.5 to 99.5 wt %, based on the total weight of the composition.

Graphic Print

In accordance with one aspect of the technology, a graphic print layer 250 is part of the stretchable circuit assembly 200 and comprises a stretchable thermoplastic or polymeric material that is biocompatible. In one aspect, the graphic print layer comprises polyurethane.

Circuit Assembly

Figure 2A:
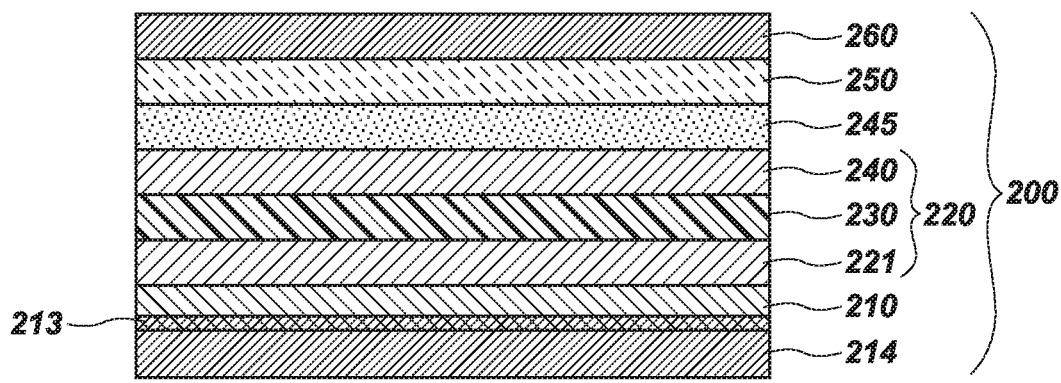
FIG. 2A is a side view of a portion of a sensor assembly in accordance with one aspect of the technology.
Figure 2B:
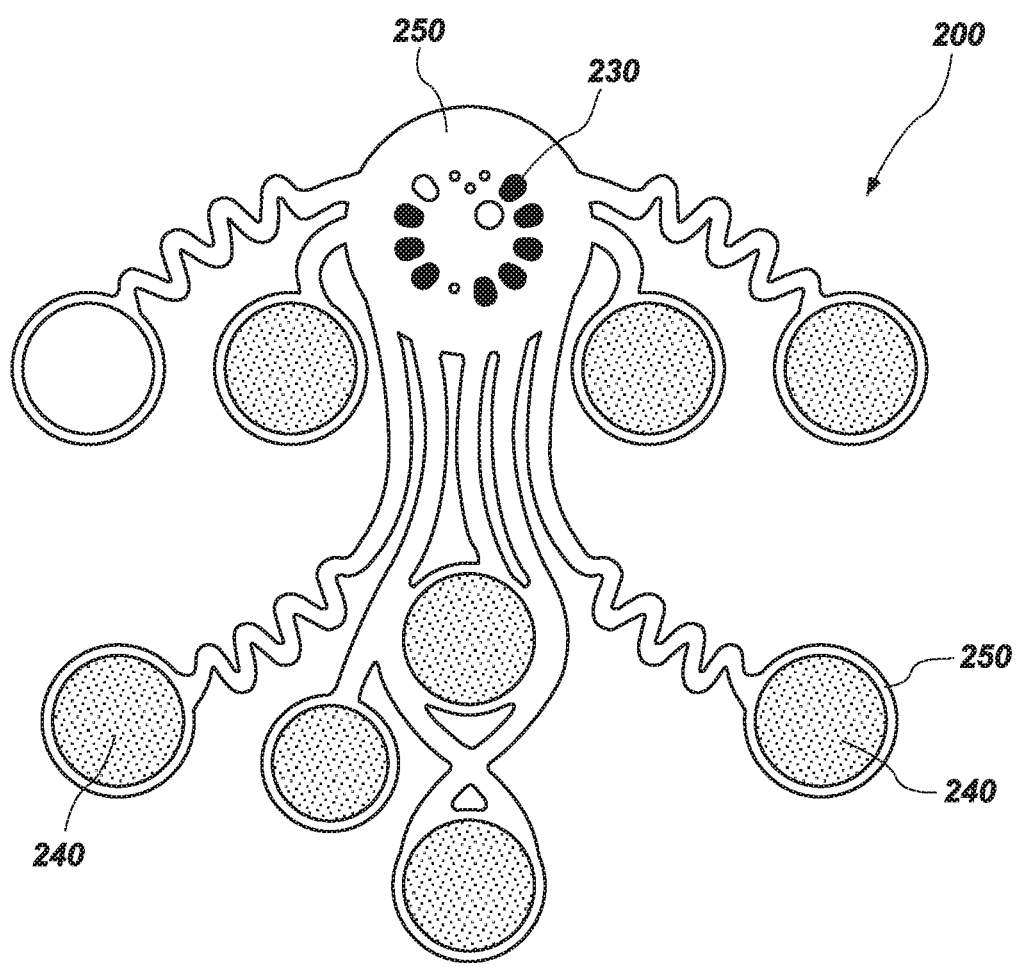
FIG. 2B is a front view of a stretchable sensor assembly in accordance with one aspect of the technology.

With reference to FIGS. 2A and 2B, generally, a stretchable circuit assembly 200 is disclosed in accordance with one aspect of the technology. The stretchable circuit assembly 200 comprises a base film 210 that comprise a substrate (e.g., a thermoplastic polyurethane film) having a hot melt adhesive disposed about one side of the substrate, the adhesive layer being covered by a paper carrier or removable film 213. An additional thermoplastic layer 214 is disposed about the adhesive layer after paper carrier or removable film 213 is removed. A conductive layer 220 is disposed about the substrate, opposite the side carrying the hot melt adhesive. The conductive assembly 220 comprise a silver layer or first conductive layer 221, a carbon layer or second conductive layer 230, and another silver layer or third conductive layer 240. The conductive assembly 220 is covered by an encapsulate 245. A graphic print layer 250 is disposed about the encapsulate 245. A final thermoplastic layer 260 is disposed atop the graphic print layer. FIG. 2A shows a side view of a portion of the circuit assembly 200. FIG. 2B shows a front view of a circuit assembly 200 cut to a pattern ready for application to a fabric. Multiple layers are shown in FIG. 2a but it is understood that al layers need not be present in all parts of the assembly and more or fewer layers may be present in different components of the assembly 200 without departing from the scope of the technology.

Figure 3:
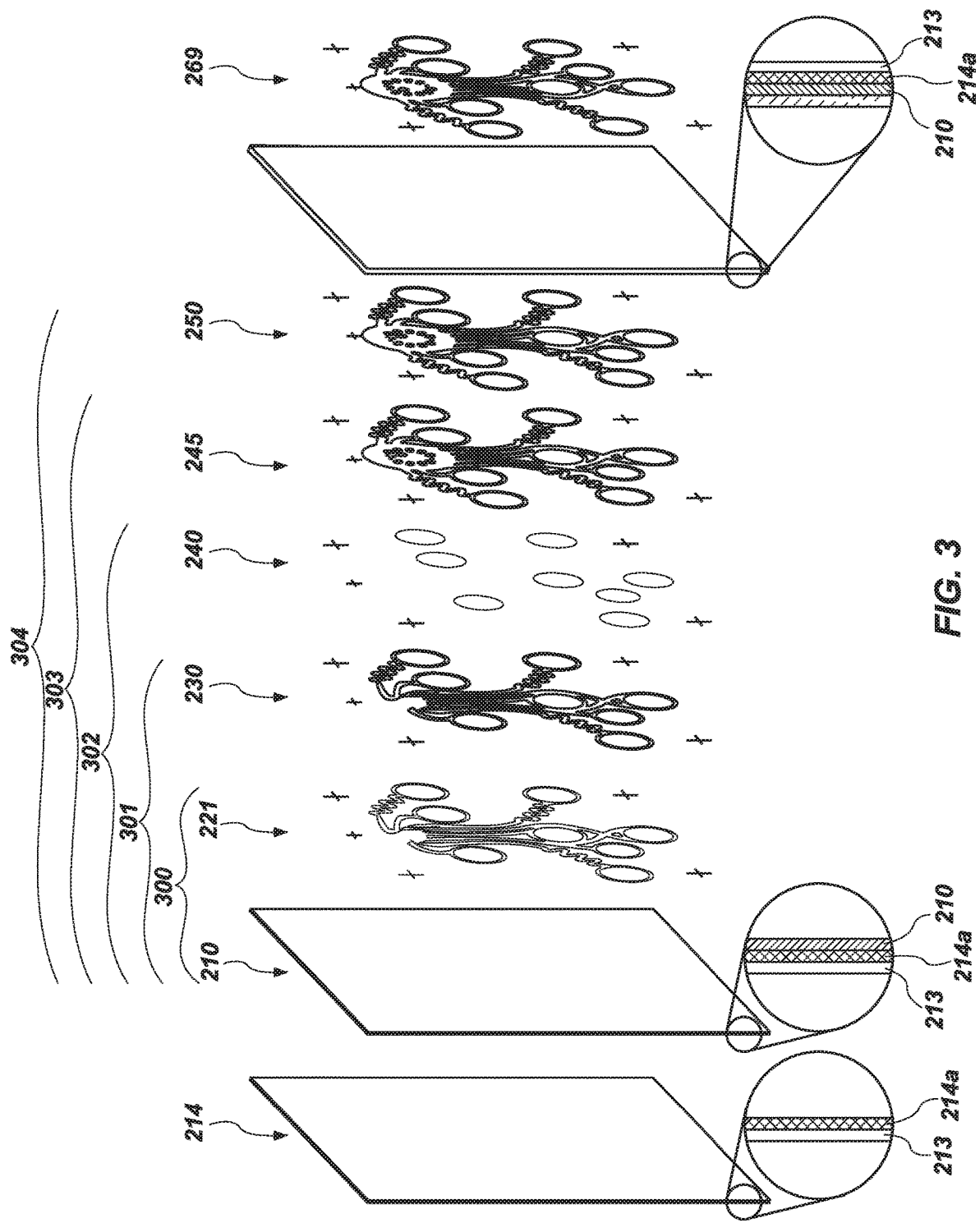
FIG. 3 is a diagram illustrating aspects of the assembly of a stretchable sensor assembly in accordance with one aspect of the technology.
Figure 4:
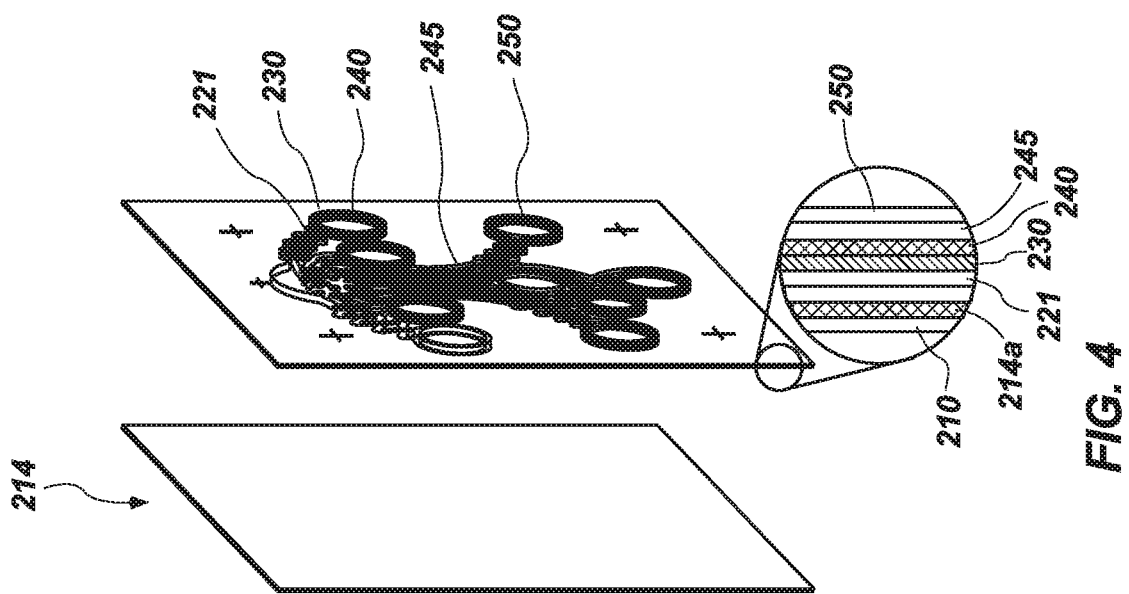
FIG. 4 is a diagram illustrating aspects of the assembly of a stretchable sensor assembly in accordance with one aspect of the technology.
Figure 5:
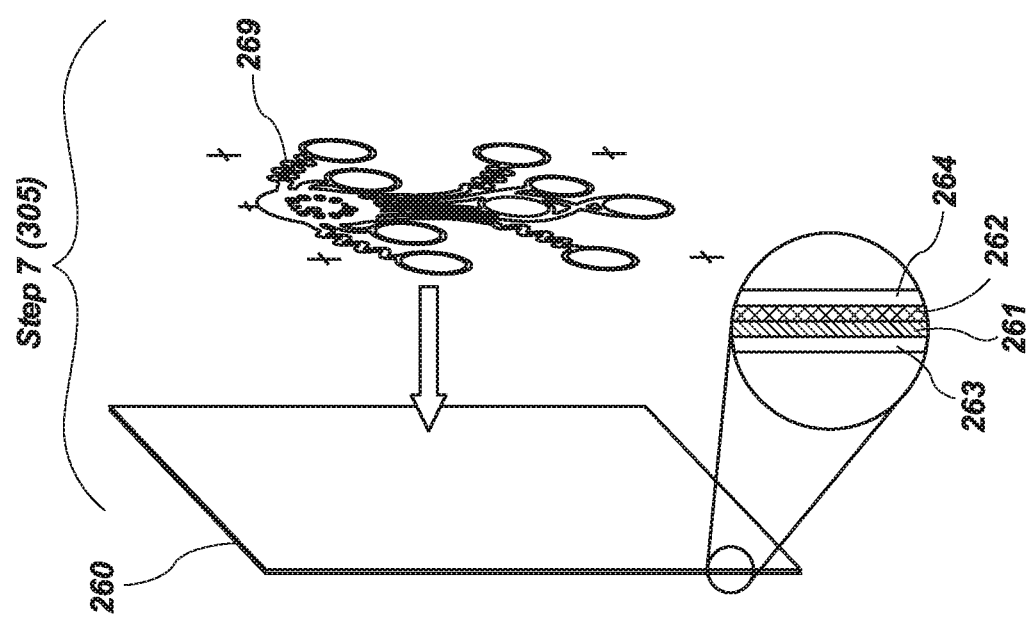
FIG. 5 is a diagram illustrating aspects of the assembly of a stretchable sensor assembly in accordance with one aspect of the technology.
Figure 6:
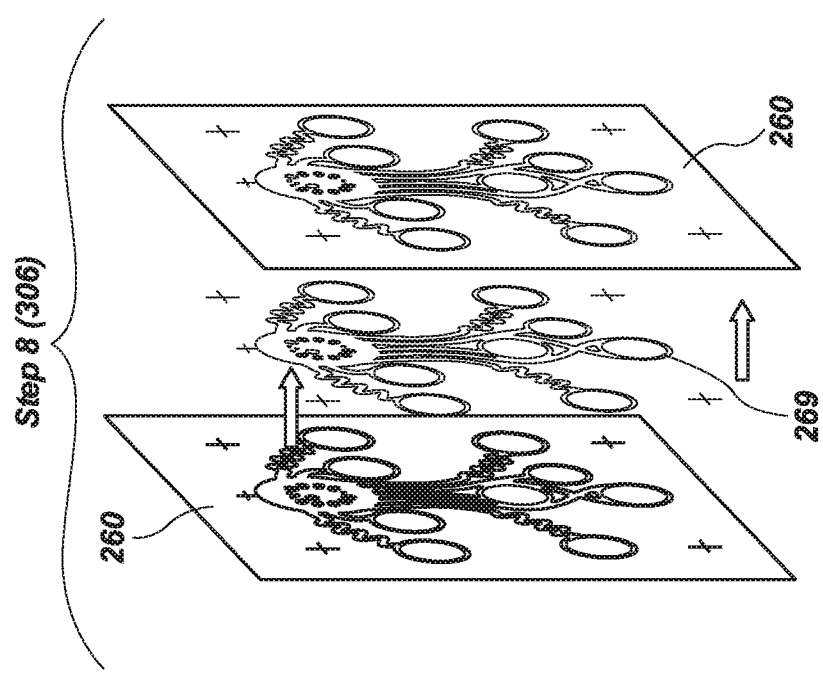
FIG. 6 is a diagram illustrating aspects of the assembly of a stretchable sensor assembly in accordance with one aspect of the technology.
Figure 7:
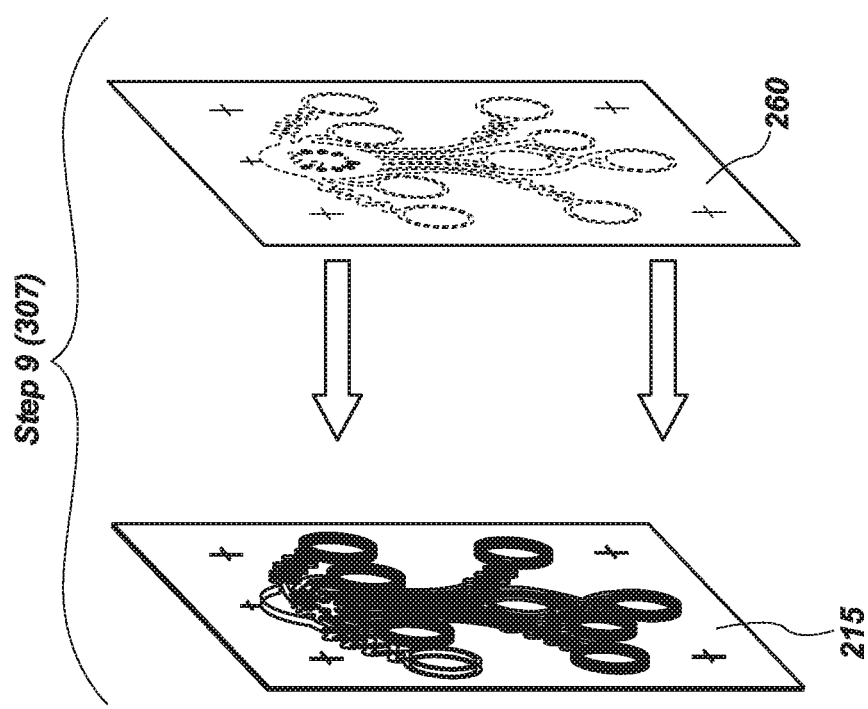
FIG. 7 is a diagram illustrating aspects of the assembly of a stretchable sensor assembly in accordance with one aspect of the technology.
Figure 10:
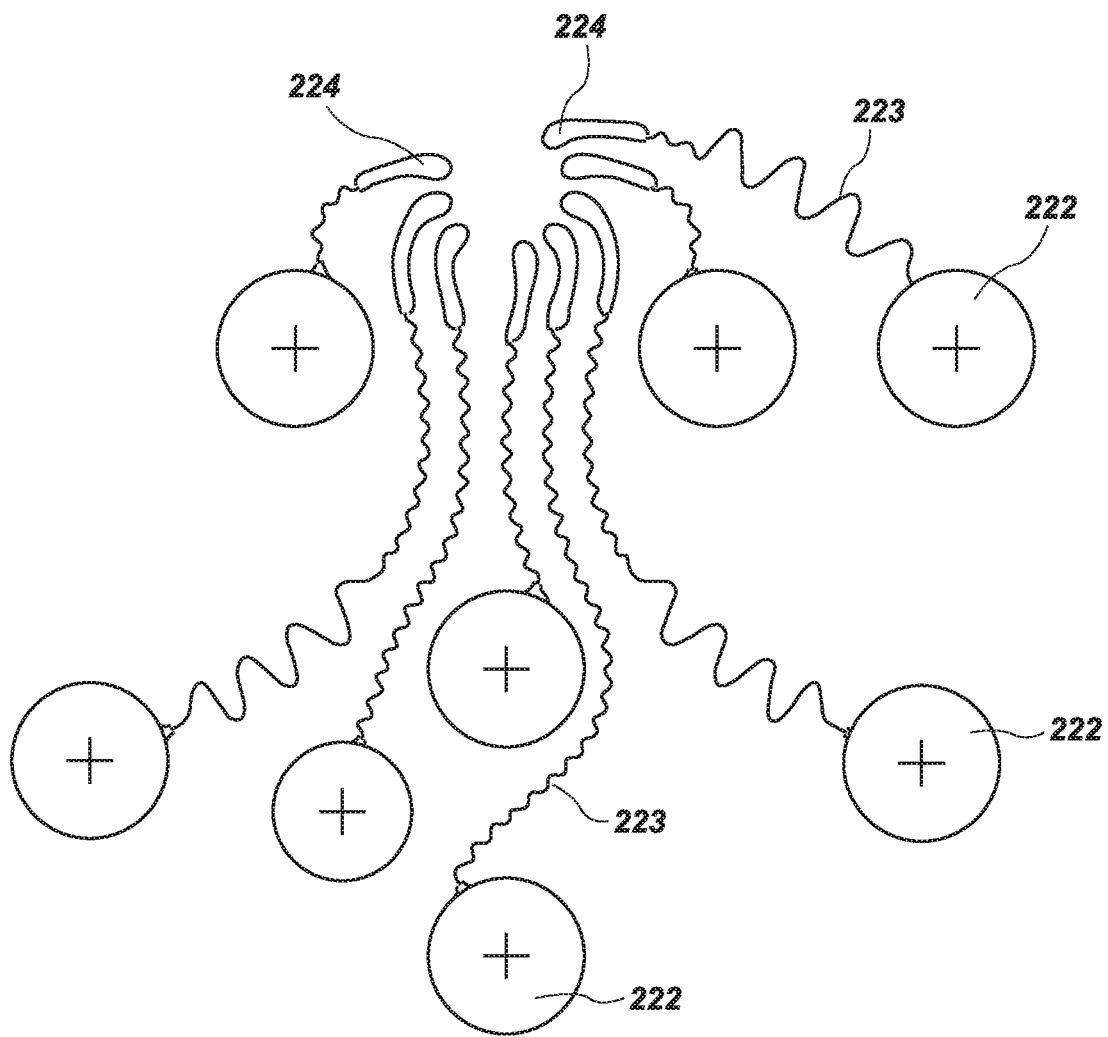
FIG. 10 is a top view of a conductive layer of a stretchable sensor assembly in accordance with one aspect of the technology.

Generally described as steps 1 through 5, the stretchable circuit assembly 200, and steps related to manufacture of the stretchable circuit assembly 200, are illustrated in accordance with one aspect of the technology. With reference generally to FIGS. 3, 4, and 10, in one aspect, at step 1 (300) the base film 210 is disposed in a printer where a first conductive layer 221 is deposited (e.g., printed or otherwise placed, etc.) on the base film 210. In one aspect, the first conductive layer comprises depositing or placing two layers of a silver composite in the pattern shown on FIG. 10. The first conductive layer 221 comprises the depositing or placing of base sensors 222 and conductive traces 223 leading back to conductive leads 224 that will couple to a monitor controller 150. In one aspect, the conductive traces 223 are oriented in a zig zag, serpentine, or sinusoidal pattern which allow the traces to flex or stretch in the longitudinal direction of the traces allowing for expansion of the maternal belly. In one aspect, the frequency of the sinusoidal pattern is consistent, meaning the height of the pattern remains about the same along the entire pathway of the trace. In another aspect, the height of the pattern varies depending on the location of the trace and its anticipated stretch during growth of the maternal belly.

Figure 11:
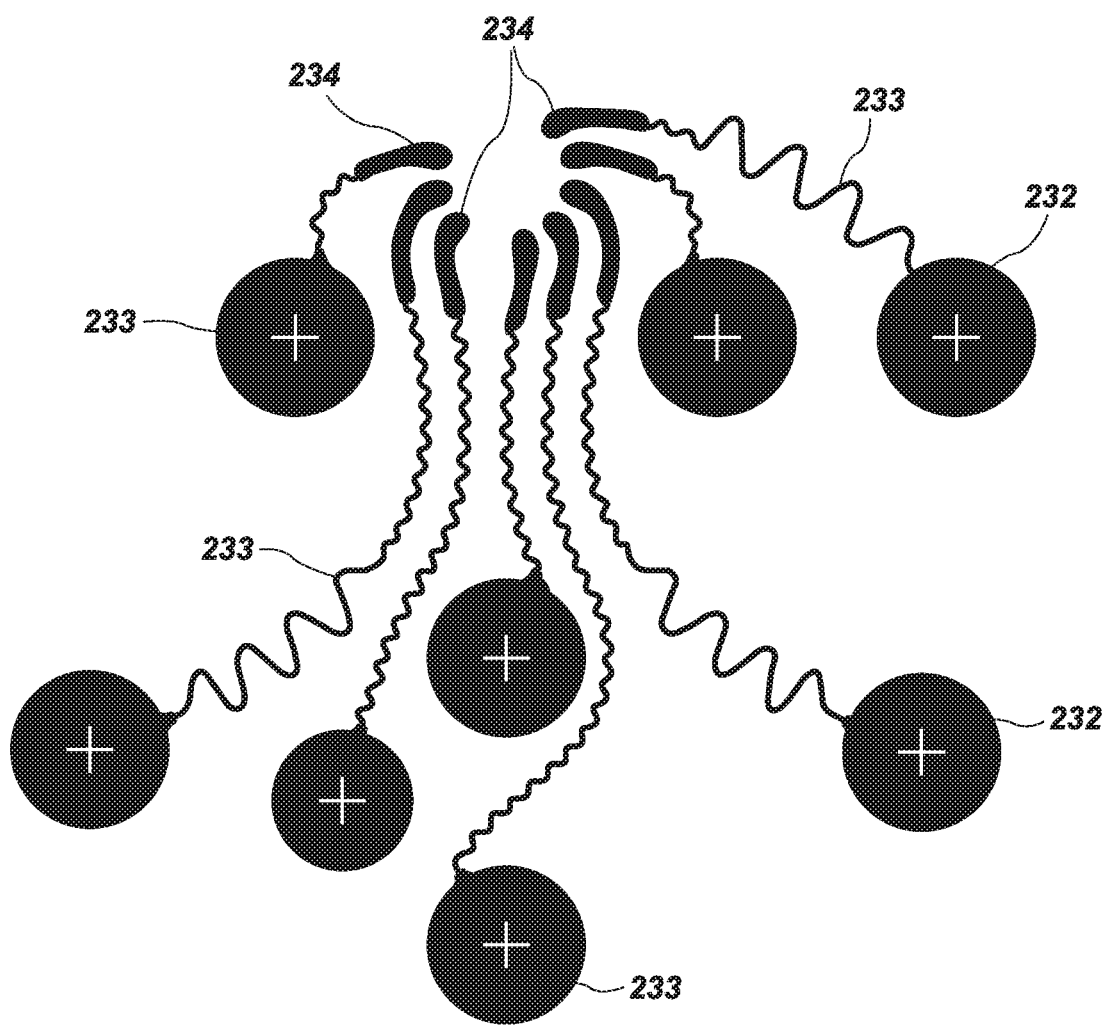
FIG. 11 is a top view of a conductive layer of a stretchable sensor assembly in accordance with one aspect of the technology.
Figure 12:
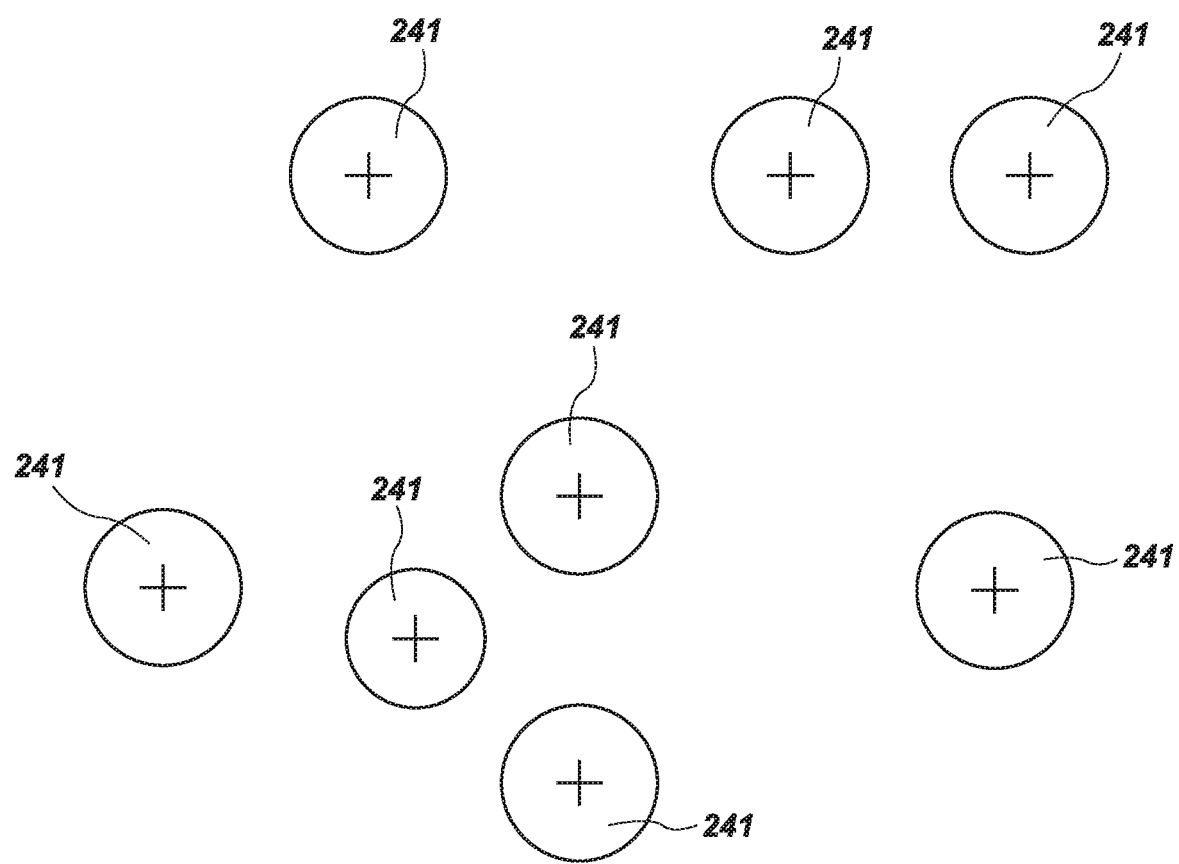
FIG. 12 is a top view of a conductive layer of a stretchable sensor assembly in accordance with one aspect of the technology.

At step 2 (301), a second conductive layer 230 is printed on top of the first conductive layer. In one aspect, the second conductive layer 230 comprises printing two layers of a carbon composite in the pattern shown on FIG. 11. The second conductive layer 230 comprises base sensors 232 and conductive traces 233 leading back to conductive leads 234. The second conductive layer 230 has a width that is larger than the width of the first conductive layer 221 and entirely covers the first conductive layer 221. At step 3 (302), a third conductive layer 240 is disposed about the second conductive layer 230. In one aspect, the third conductive layer 240 comprises a silver composite that is printed only on top of the sensor locations 241 forming a multiple layer sensor 280 (i.e., silver/carbon/silver) as shown on FIG. 12. Advantageously, the multi-layered sensor or electrode construction provides an optimized amount of resistance to the electrical signals sent into the sensor while adequately generating useable information for the device 50. In one aspect of the technology, the sensor 280 has a resistance value ranging between 9 and 11 ohms.

While a specific construction of the multiple layer sensor is described, it is understood that any number of different materials may be used. Moreover, less than three layers or more than three layers may be used to create the sensors.

Figure 13:
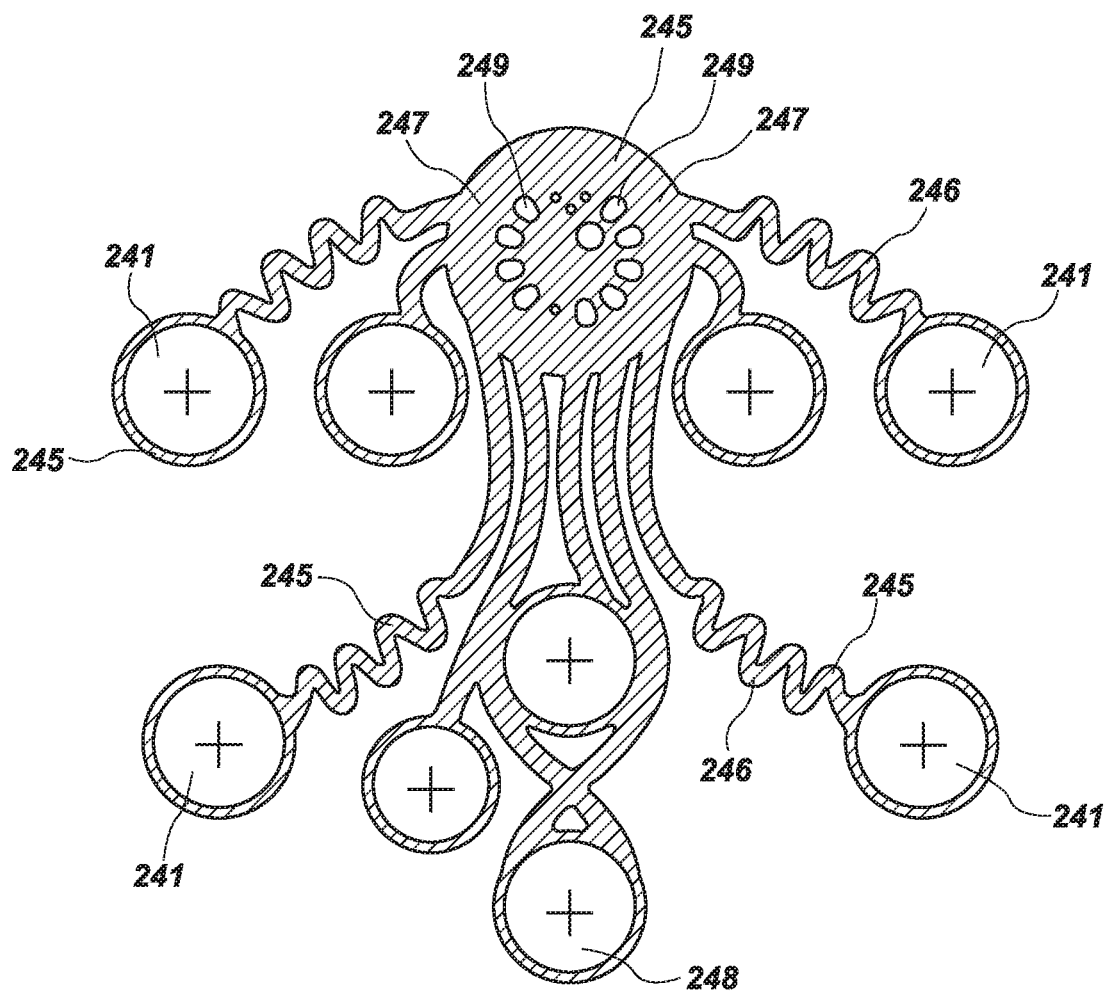
FIG. 13 is a top view of an encapsulating layer of a stretchable sensor assembly in accordance with one aspect of the technology.
Figure 14:
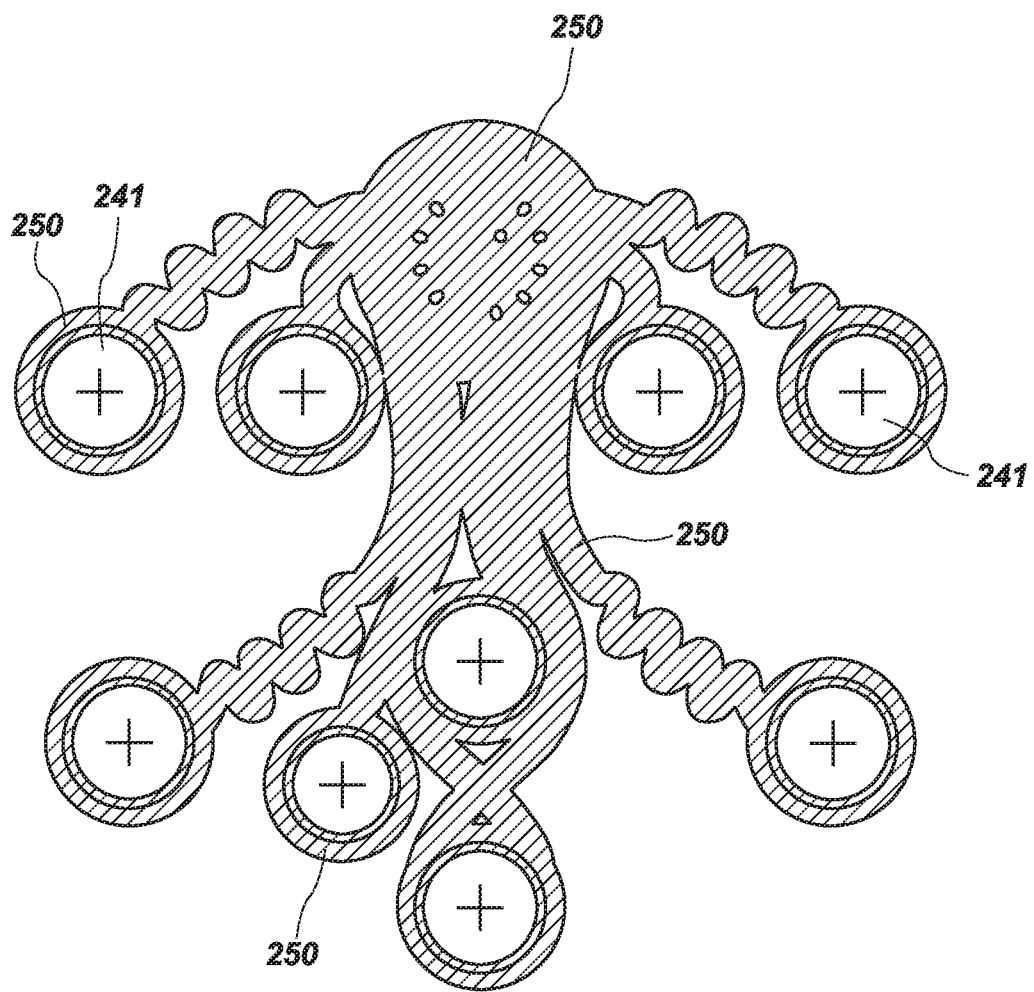
FIG. 14 is a top view of a graphic print layer of a stretchable sensor assembly in accordance with one aspect of the technology.
Figure 15:
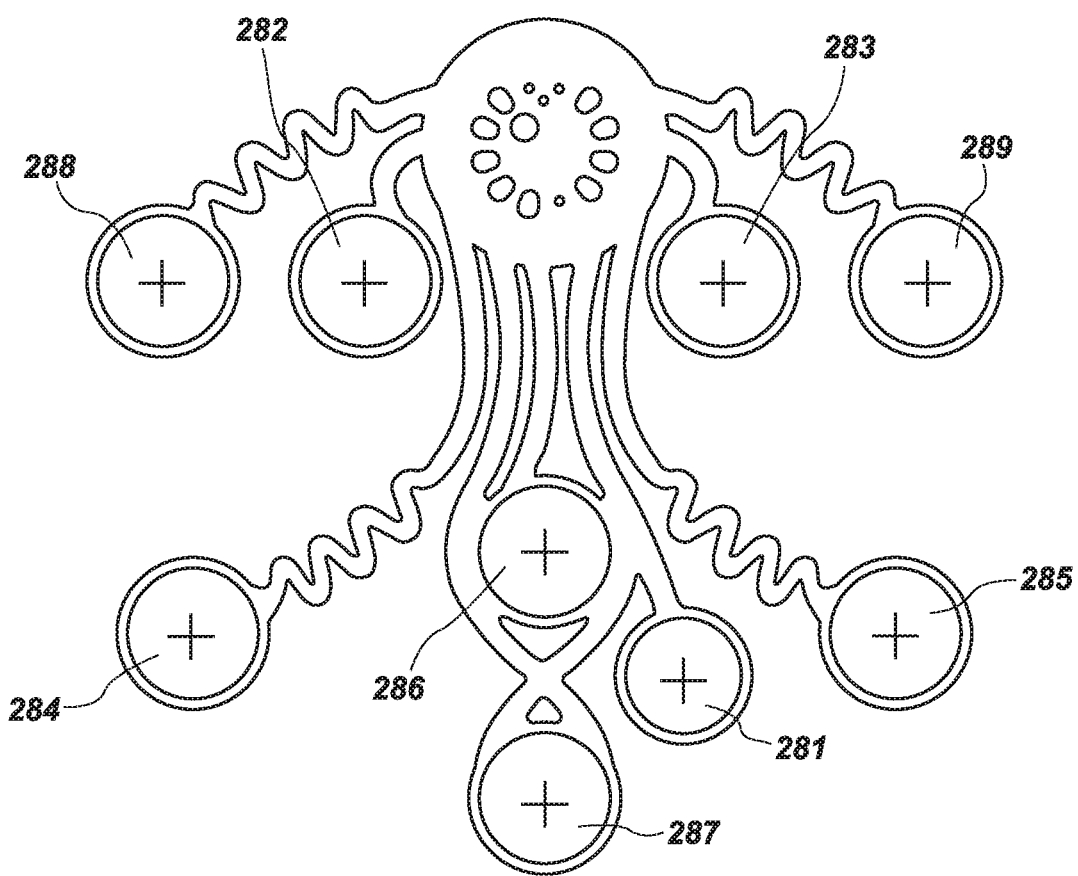
FIG. 15 is a top view of a graphic cover cut line of a stretchable sensor assembly in accordance with one aspect of the technology.
Figure 16:
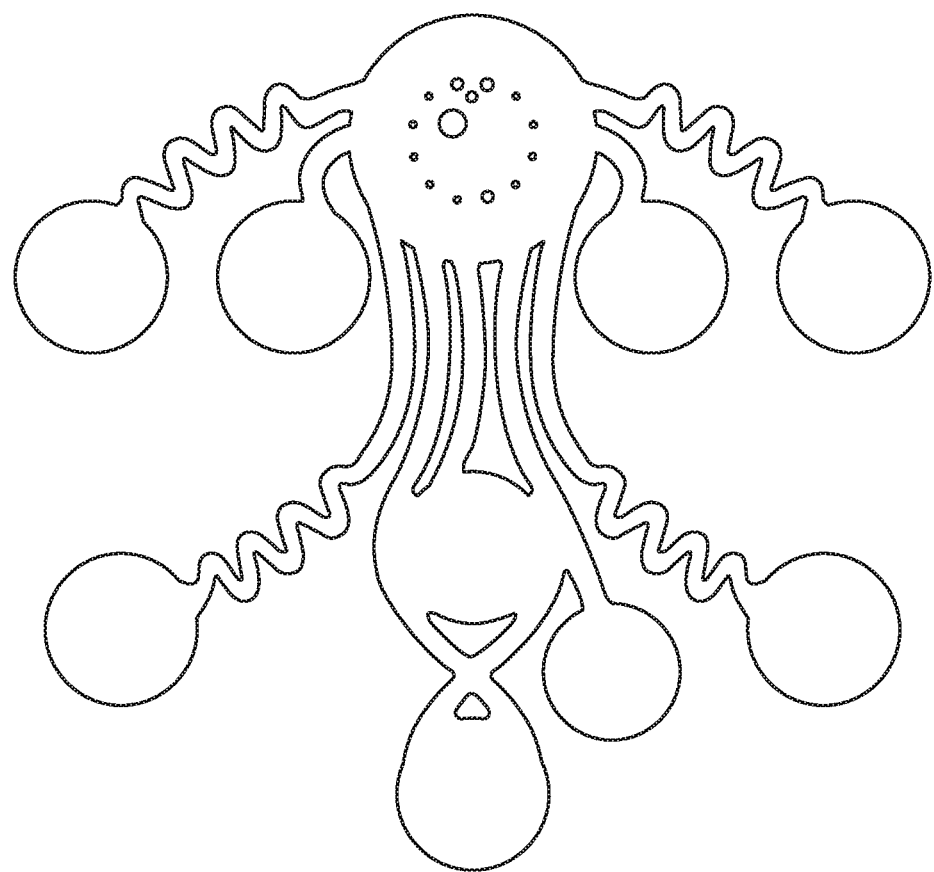
FIG. 16 is a top view of a finished cut line of a stretchable sensor assembly in accordance with one aspect of the technology.

At step 4 (303), after the conductive layer or subassembly 220 is disposed or printed on the base film 210, an encapsulating layer 245 is disposed or printed about the top of portions of the conductive assembly 220. In one aspect, the encapsulating layer comprises two layers of the encapsulating composition wherein the composition covers the traces (at 246) and a portion of the leads (at 247) of the conductive assembly 220 but leaves the sensor assembly exposed so that it may contact the skin of the expectant mother. The encapsulating layer encircles the sensors 248, but does not cover them as shown in FIG. 13. It also leaves a portion of the conductive leads exposed at 249. At step 5 (304), a graphic print layer 250 is printed on top of the encapsulating layer 240 covering the encapsulating layer in its entirety leaving portions of the sensors and leads exposed as shown in FIG. 15. In one aspect of the technology, the graphic print layer 250 is colored to match or be substantially equivalent to the color of the fabric of the garment 100.

With reference now to FIGS. 5 through 10 generally, a cover film 260 or thermoplastic layer is prepared at step 7 (305) for application to the prepared substrate in steps 1 through 6. The cover film 260 comprises a thermoplastic polyurethane layer 261 with a hot melt adhesive 262 on one side and removable carrier films or papers 263, 264 on opposite sides of the film 260. At step 8 (306), a cut line 269 is established and the cover film 260 is cut according to the established pattern through the back side of the carrier paper 264, layer 261 and 262 but not through the carrier paper 263. Excess paper and material are removed from the cover film 260 and the cover film 260 is applied to the prepared substrate assembly 215. That is, the cover film 260 is applied to the base film 210 with the conductive assembly 220, encapsulating layer 245 and graphic print 250 disposed or printed thereon. At step 9 (307), the cover film 260 is placed in contact with the prepared substrate assembly 215 so that the respective patterns of the cover film 260 and prepare substrate assembly 215 are aligned.

Figure 8:
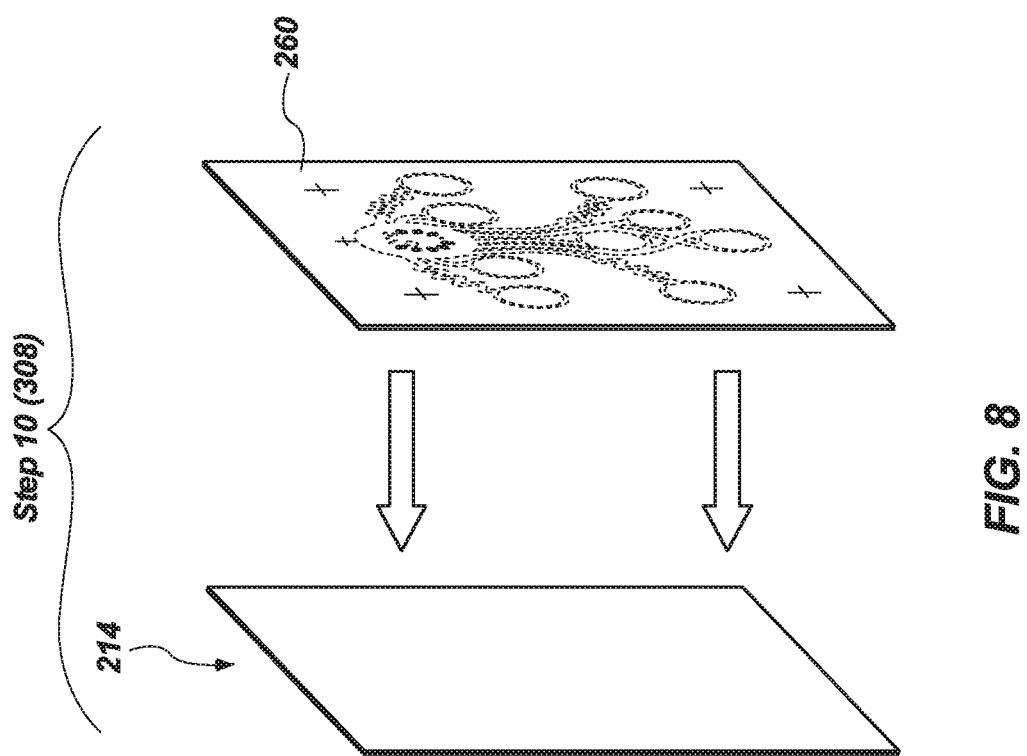
FIG. 8 is a diagram illustrating aspects of the assembly of a stretchable sensor assembly in accordance with one aspect of the technology.
Figure 9:
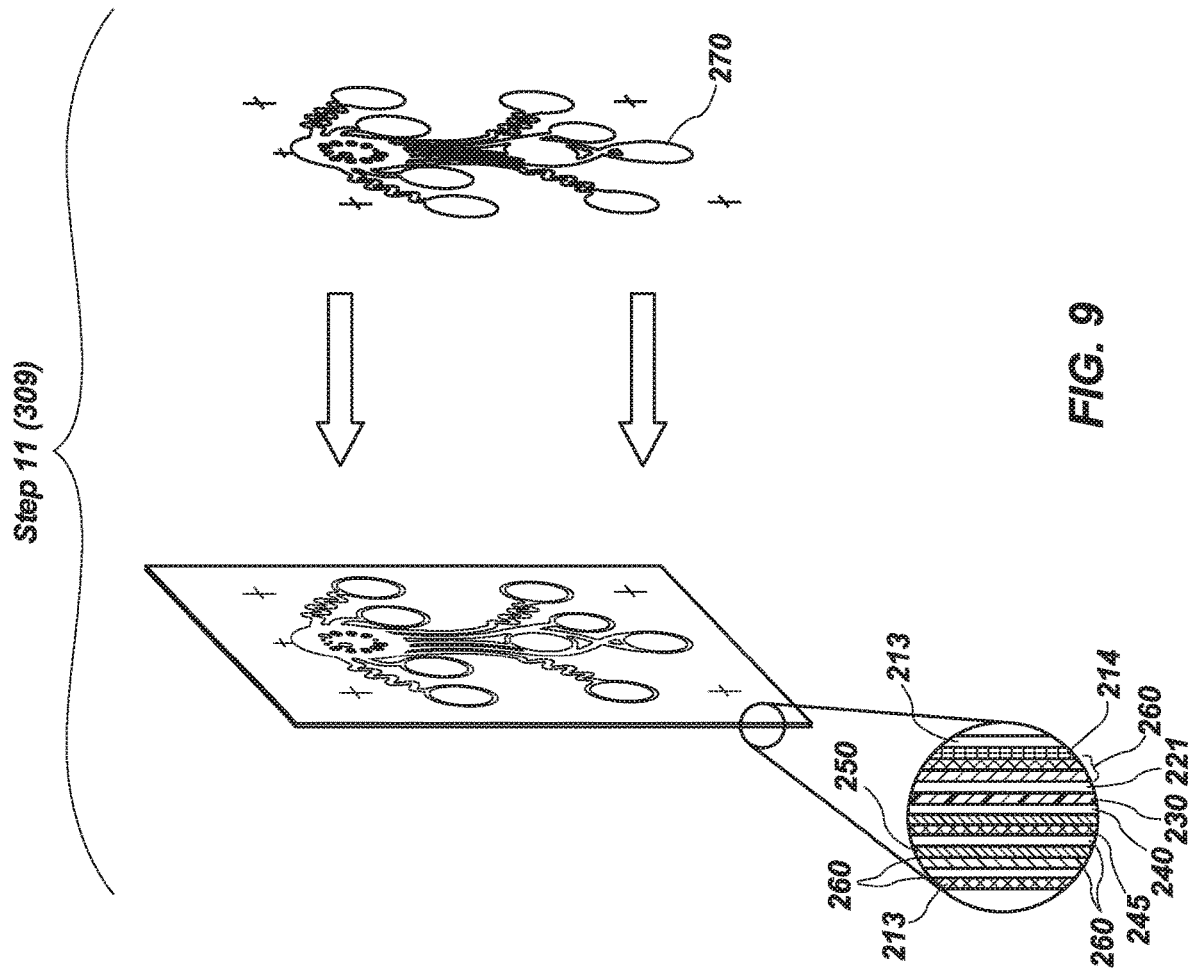
FIG. 9 is a diagram illustrating aspects of the assembly of a stretchable sensor assembly in accordance with one aspect of the technology.

At step 10 (308), the carrier paper 263 is removed from the cover film 260 and is disposed in contact with the thermoplastic layer 214. The final assembly is then cut according to the final cut line 270 at step 11 (309) as shown in FIG. 8 to produce a completed sensor assembly 300 for application to a piece of fabric. Specifically, in accordance with one aspect of the technology, for placement on the front piece 1110 of garment 100. The final cut is placed through the different layers of the final assembly except for the final carrier film 213. In one aspect of the technology, the completed sensor assembly 300 has a total thickness ranging from about 0.35 to about 0.50 mm.

It is noted that no specific order is required in the steps described above unless specifically required by the claims set forth herein, though generally in some aspects of the technology, the method steps can be carried out sequentially.

Figure 17:
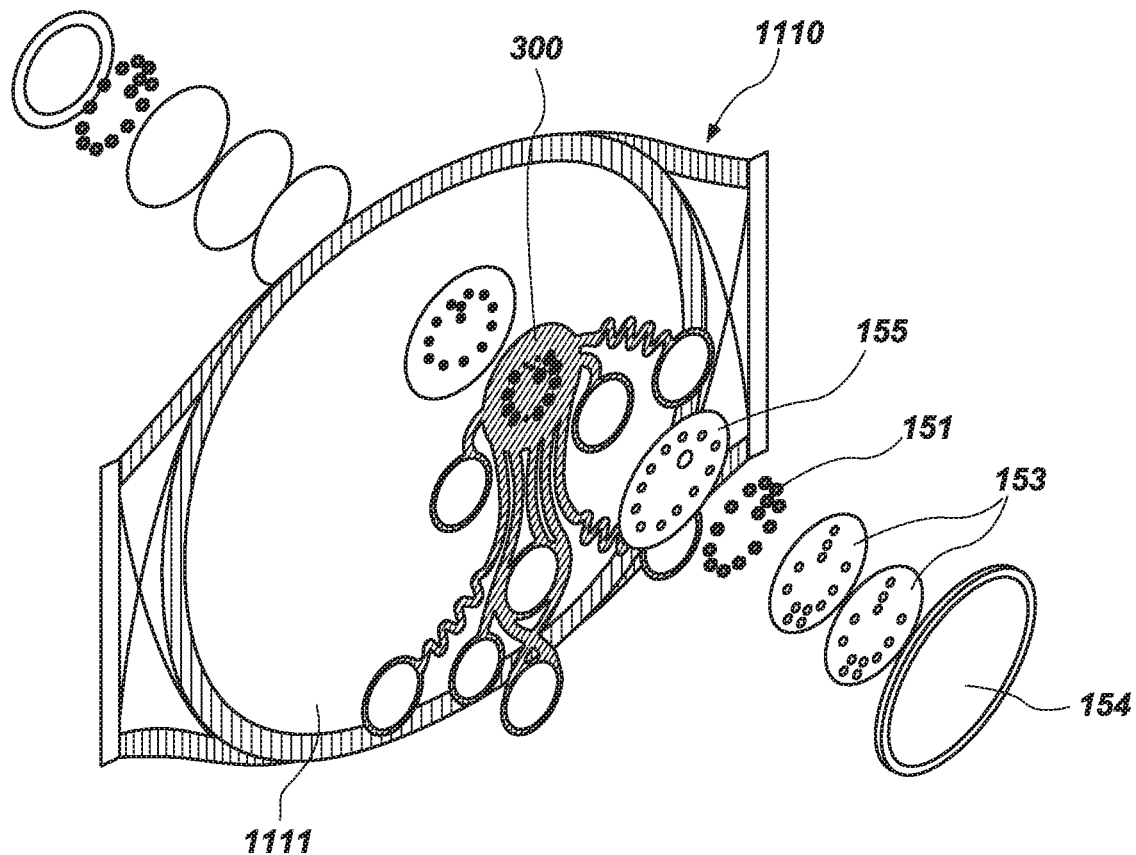
FIG. 17 is an exploded view of the assembly of a wearable prenatal monitor in accordance with one aspect of the technology.

With reference to FIG. 17, in one aspect of the technology, the sensors are strategically sized and located about the abdomen of the mother to optimize the information that is gathered. In one aspect of the technology, sensor 282 and 283 are disposed about either side of monitor controller 150 and are positioned proximate to the uterus of the mother when worn by the expectant mother. These sensors (282 and 283) are optimally located to receive information related to the contractions of the mother. Sensors 284, 285, 286, and 287 are optimally located to receive information about the position of the head of the baby. More specifically, sensors 284, 285, 286, and 287 operate to measure the QRS signal of the heart of the baby. The sensors compare the differences in the QRS signal (e.g., the polarity of the signal, among other things) measured from sensor to sensor to determine the position of the head of the baby in-utero. Sensors 282 and 283, as well as additional reference sensors 288, 289 are used in connection with sensors 284, 285, 286, and 287 to further refine the position of the head of the baby. The sensors are approximately 1 to 1.5 inches in diameter to optimize the number of sensors capable of being placed on the abdomen of the mother against the maximum amount of sensor surface area. Sensors 286 and 287 are optimally placed about the bottom of the abdomen to be near the top of the pubic bone of the mother and just below the belly button. In one aspect of the technology, sensor 286 and 287 are approximately 2.5 to 3 inches apart from center to center. Sensor 281 is used as a ground electrode.

Figure 18A:
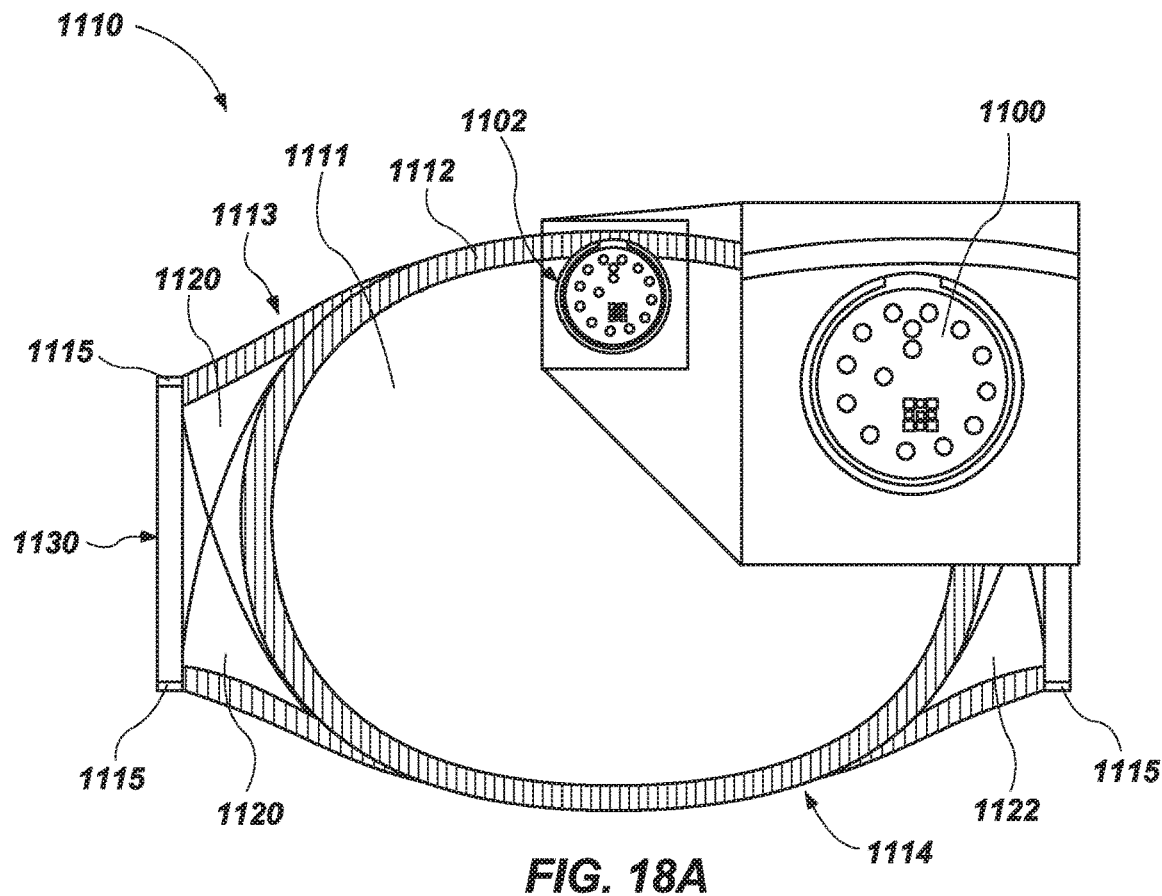
FIG. 18A is a front view of a sensor panel and portion of a sensor module disposed thereon in accordance with one aspect of the technology.
Figure 18B:
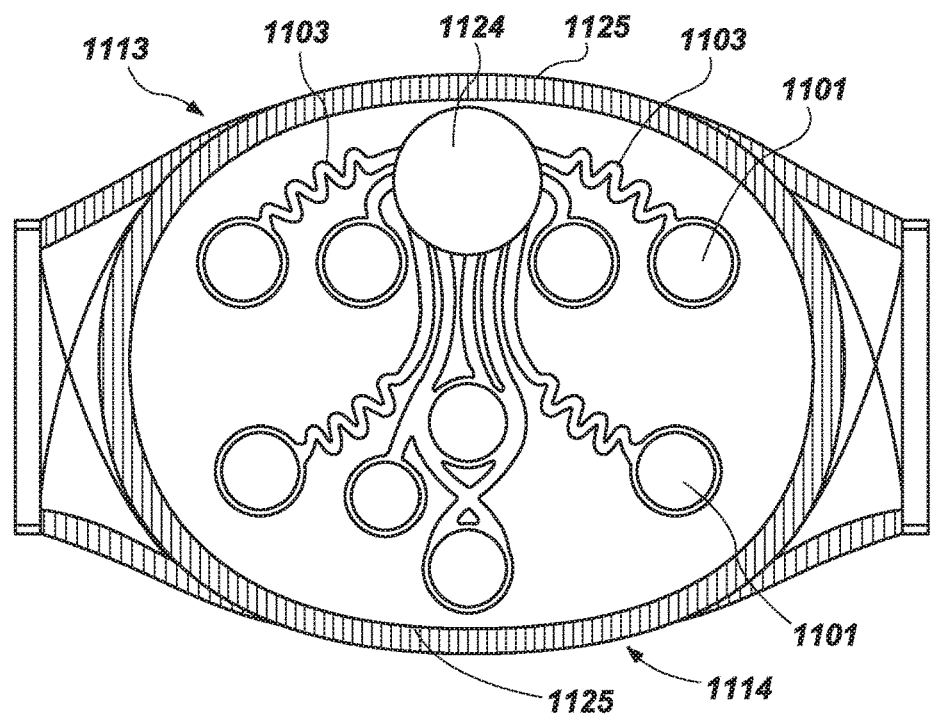
FIG. 18B is a front view of a sensor panel in accordance with one aspect of the technology.

With reference generally to FIG. 1 and FIG. 18, the completed sensor assembly 300 is disposed about a "skin side" of the front piece 1110 of garment 100 and heat treated under applied pressure to couple the sensor assembly 300 to the garment 100. Monitor controller 150 is formed about a top portion of the sensor assembly 300 where the leads are disposed in a circular pattern in order to couple with portions of the monitor controller 150. A "skin-side" portion of the monitor controller 150 comprises a printed circuit board 155 coupled to the collection of leads via a plurality of nuts, though other connection mechanisms may be used as is known in the art. A leveling plate 153 is adhered to the printed circuit board and a piece of backing fabric 154 is disposed about the entire "skin-side" portion of the monitor controller 150. A portion of the monitor controller 150 that is disposed about the outside portion or opposite the skin of the expecting mother comprises a mother board enclosure coupled to a plastic pad that is adhered to the fabric of garment 100.

The printed circuit board contains memory and programming instructions for storing information used for performing delivering a signal to the sensors and record data receive from the sensors. Memory refers to electronic circuitry that allows information, typically computer data, to be stored and retrieved. Memory can refer to external devices or systems, for example, disk drives or other digital media. Memory can also refer to fast semiconductor storage, for example, Random Access Memory (RAM) or various forms of Read Only Memory (ROM) that are directly connected to the processor. Computer terminals represent any type of device that can access a computer network. Devices such as PDA's (personal digital assistants), cell phones, personal computers, lap top computers, tablet computers, mobile devices, or the like could be used to access information produced by the monitor controller 150. The computer terminals will typically have a display device and one or more input devices. The network may include any type of electronically connected group of computers including, for instance, Internet, Intranet, Local Area Networks (LAN), or Wide Area Networks (WAN). In addition, the connectivity to the network may be, for example, remote modem or Ethernet.

The above description provides numerous specific details for a thorough understanding of the embodiments described herein. However, those of skill in the art will recognize that one or more of the specific details may be omitted, or other methods, components, or materials may be used. In some cases, operations are not shown or described in detail. Furthermore, the described features, operations, or characteristics may be combined in any suitable manner in one or more embodiments. It will also be readily understood that the order of the steps or actions described in connection with the embodiments disclosed may be changed as would be apparent to those skilled in the art.

As will be appreciated by one skilled in the art, aspects of the present invention may be embodied as a system, method or used with a computer program product as part of a prenatal monitoring device. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized in recording and reporting the data collected from the device 50. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, blue tooth, etc., or any suitable combination of the foregoing. Computer program code for carrying out operations for aspects of the present technology may be written in any combination of one or more programming languages, including an object oriented programming language such as Java, Visual Basic, SQL, C++ or the like and conventional procedural programming languages, such as the "C" programming language or similar programming languages. The program code may execute entirely on a user's computer, partly on the user's computer, as a stand-alone software package, partly on the user's computer and partly on a remote computer, entirely or partly within a monitor controller, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Referring generally to FIGS. 19-23, a wearable prenatal monitoring device is disclosed. The device is intended to be worn from approximately 17 weeks of pregnancy until full term, or as directed by a medical practitioner. Fabric is cut to a pattern and assembled into a garment that is configured to closely fit the contours of an expectant mother and to be configurable with her changing contours throughout the course of the pregnancy. In one aspect of the technology, the fabric of the garment may be a stretchable fabric, for example a woven elastomer in the class of segmented co-polyesters such as polyester-polyurethane copolymer fibers alone or blended with cotton or other natural fibers or synthetic polymer fibers such as polyester, nylon, acrylic, and the like. For example, in one aspect of the technology, the fabric of the garment comprises a nylon, polyester, spandex blend. The fabric is configured to wrap around the body of the mother and couple to itself using hook and loop fasteners, snaps, zippers, belts, or other fasteners known in the art. In one aspect of the technology, a hook and loop fastener is used wherein the distal end of the hook is cushioned by a wide loop pad. That is, the base of the loop is wider than the hook which minimizes the likelihood that the hook will contact the underlying fabric.

In one aspect of the technology, the garment comprises one or more separate pieces configured to be coupled together when worn by the user or pressed against the abdomen. In one aspect, the garment comprises a front piece or front panel 1110 that carries the electronics, sensors, and related materials used to monitor maternal and prenatal data. The garment further comprises a back piece or back panel 1200 that couples to the front piece or front panel 1110 and is intended to provide a support mechanism for holding the front piece 1110 firmly against the abdomen of the expectant mother. While two pieces are referenced herein, it is understood that the garment may comprise a single integrated piece of fabric or multiple pieces of fabric as suits a particular application.

The garment is provided with a plurality of electrodes 1101 integrated or coupled to the fabric. Namely, a ground electrode GND and a plurality of abdominal electrodes are disposed about the garment in the area that is configured to fit about the abdomen of the expectant mother. The ground electrode may be located anywhere on the body. A monitor controller 1102 is electrically coupled to the electrodes 1101 by way of a plurality of conductive pathways 1103. The monitor controller 1102 receives the signals from the conductive pathways 1103 and electrodes 1101 and processes the signals. In one aspect, the monitor controller 1102 comprises a removable top piece 1102a having a plurality of retractable pins 1105 configured to mate with conductive plates 1106 disposed in a fixed base 1102b. The monitor controller comprises a power source (e.g., a battery) and hardware configured to process signals received from the conductive pathways 1103. The fixed base 1102b is secured to an area where the conductive pathways converge. These conductive pathways 1103 may be embodied in the form of conductive wires or conductive film incorporated into the garment fabric or otherwise coupled or adhered to the fabric. In one aspect, the removable top piece and the fixed base 1102b are configured to mechanically couple together and have a positive and negative magnetic connection to facilitate removal of the top piece. In one aspect, the top piece comprises a rechargeable battery and recharging base. If the expectant mother wishes to recharge the battery without removing the garment, she may remove the top piece 1102a and place it on the recharging base. Removal of the top piece 1102a is also important prior to washing the garment in order to protect the electronics therein.

Generally speaking, the non-ground electrodes are intended to measure the contractions of the expectant mother and the heartbeat of her baby. The electrodes near the top of the abdomen are generally responsible for the detection of contractions while the electrodes near the bottom of the abdomen are responsible for detection of the heartbeat of the baby. Other data, of course, is gathered regarding the health of the mother and the baby, including the maternal heart rate, the general sleep position of the mother (e.g., sleeping on front, back, or side, etc.), and general movement of the baby (e.g., kicking, breathing or movement of the fetal diaphragm, hiccups, etc.).

While general reference is made to the primary responsibility of certain of the electrodes in terms of their data gathering function, it is understood that all of the electrodes work in tandem to gather useable information. In certain aspects of the technology, the comparison of different data points collected over time by the different electrodes is used to provide useful information to the expectant mother and/or her medical care provider or other interested persons. Moreover, other sensors can be used and incorporated into the garment or monitor controller 1102 to gather additional information, including pulse oximeters, accelerometers, and the like.

Broadly speaking, in one aspect of the technology, the conductive pathways comprise a base film coupled to a conductive material to form a stretchable conductive pathway. In one aspect of technology, the base film comprises a polymer thick film composition for use in electrical circuits and, in particular, highly stretchable deformed circuits such as those applications where functional circuitry is generated on fabrics for clothing. Conductive material is printed and dried on a substrate (e.g., the base film) so as to produce a functioning circuit wherein the entire circuit is subjected to the typical bending/creasing that a fabric would experience about the abdomen of an expectant mother. Aspects of the technology limit stretching of the fabric that is coupled to the electrical circuits while providing comfortable stretch and support to the maternal belly and the changing maternal shape.

In one aspect of the technology, the front piece 1110 (e.g., the portion of the device housing the electrodes), comprises a generally circular or oval main panel 1111 comprising a first material configured to conform, at least in part, to the shape of the maternal abdomen. In one aspect, the main panel 1111 is cut and shaped to have a generally concave shape that is shown, for example, at 1190 in FIG. 20B. In one aspect, the main panel 1111 is circumscribed, at least in part, by a second material 1112. The second material 1112 also extends about a top 1113 and bottom 1114 portion of the front piece 1110 and terminates at the connecting edges 1115 of the front piece 1110. A back side 1118 of the front piece 1110 comprises a reinforcing material disposed adjacent to the second material 1112 as it extends about the top 1113 and bottom 1114 of the front piece 1110.

In one aspect of the technology, the front piece 1110 further comprises a third material 1116 disposed laterally from the side of the main panel 1111 extending towards the connecting edges 1115. In one aspect, the third material 1116 tapers inwardly in the direction from the main panel 1111 towards the connecting edges for a predetermined length and then tapers outwardly until it couples to the connecting edge 1115. In one aspect, the third material 1116 tapers to a point 1117 creating a hinge or pivot point facilitating movement and enhanced comfort for the expectant mother. The hinge point 1117 directs forces that tighten the main panel 1111 about the maternal abdomen to a lateral side of the abdomen. In one aspect of the technology, a fourth material 1120 is disposed above 1121 and below 1122 the tapering third material 1116 and further within the second material 1112 which is disposed about the top and bottom side of the front piece 1110.

While a plurality of different materials in different shapes is disclosed, it is understood that a variety of different combinations are contemplated herein without departing from the scope of the technology. For example, in one aspect of the technology, the front piece 1110 comprises a main panel 1111 circumscribed by a second material 1112 only. In another aspect, the front piece comprises a main panel 1111 having a second material 1112 and a third material 1113 that does not taper from the second material to the connecting edge 1115 but rather extends within the perimeter created by the second material 1112. In yet another aspect, the main panel 1111 extends laterally towards the connected edge 1115 in the location where the second material 1112 and third materials 1116 are shown on the figures. In yet another example, the front piece comprises a main panel 1111 of an isotropic material and a lateral side with an anisotropic material extending from the lateral edge of the main panel 1111 to the connecting edge 1115 with no intervening fabric between the main panel 1111 and the fabric extending between the main panel 1111 and the connecting edge 1115. In other words, there are numerous different combinations of materials and shapes of materials that are contemplated herein to enable stretching of the main panel 1111 for a form fit about the maternal abdomen while limiting stretching about the sides of the main panel 1111, and no specific disclosure should be construed as limiting the scope of the technology.

In one aspect of the technology, each of the first, second, third, and fourth materials comprise different types of materials or knit styles resulting in a different stretchability. During pregnancy, the front piece 1110 stretches more in a lateral direction than in a vertical direction to accommodate the growing maternal abdomen. Accordingly, the different materials and material configurations limit stretching at least in a lateral direction. In one aspect of the technology, the conductive pathways 1103 that extend in a lateral direction to electrodes 1101 are disposed in a zig zag, serpentine, or sinusoidal configuration to allow the conductive pathways 1103 to stretch without compromising the integrity of the electric pathway 1103. Advantageously, the main panel 1111 may be stretched tightly across the abdomen of the expectant mother without stretching the material so far that the conductive pathways 103 are damaged while the lateral sides, 1105 and 1106, of the front piece provide limited stretch, but multi-directional movement of the garment as the expectant mother moves.

In one aspect, the first material 1109 (in one aspect comprising a plain weave) has the highest rate of stretchability out of the different type of materials or knit styles. The second material 1112 (in one aspect comprising a rib knit) has the second highest rate of stretchability. The fourth material 1120 (in one aspect comprising a mini rib knit) has the third highest rate of stretchability. The third material 1113 (in one aspect comprising a cross-weave) has the fourth highest rate of stretchability. It is understood that any different combination of materials with different rates of stretchability may be used so long as the materials function to limit lateral stretching of the sensor panel, minimizing the likelihood that the underlying conductive pathways 1103 fail, while optimizing electrode 1101 contact with the maternal belly and comfort of the mother.

In aspects of the technology, materials used in connection with the fabric of the maternal garment comprise the following characteristics:

Example Embodiment 1

| | Fabric Sample Size | Stretchable Area | Inches Max Stretch Length (inches) | Max Force |
|---|---|---|---|---|
| Rib Knit | 3" × .75" | 2" × .75" | 4.625 | 7 N |
| Cross Weave | 3" × .75" | 2" × .75" | 4.25 | 2.72 N |
| Plain Weave | 3" × .75" | 2" × .75" | 5.5 | 10.2 N |
| Mixed Fabric | 3" 9 mm | 2" × 9 mm | 4.5 | 2.4 N |
| Edging (ribbed) | 3" × .75" | 2" × .75" | 6.5 | 62 N |

Example Embodiment 2

| | Fabric Sample Size | Stretchable Area | Inches Max Stretch Length | Max Force |
|---|---|---|---|---|
| Rib Knit | 3" × .75" | 2" × .75" | 4.75 | 2.4 N |
| Cross Weave | 3" × .75" | 2" × .75" | 4.6 | 1.6 N |
| Plain Weave | 3" × .75" | 2" × .75" | 5.5 | 2.2 N |
| Mixed Fabric | 3" 12 mm | 2" × 9 mm | 4.1 | 4.4 N |
| Edging (ribbed) | 3" × .75" | 2" × .75" | 6.3 | 4 N |

Example Embodiment 3

| | Fabric Sample Size | Stretchable Area | 1 Newton Force Stretch Length (Inches) | 2 Newton Force Stretch Length (Inches) |
|---|---|---|---|---|
| Rib Knit | 3" × .75" | 2" × .75" | 2.75 | 3.5 |
| Cross Weave | 3" × .75" | 2" × .75" | 3 | 4 |
| Plain Weave | 3" × .75" | 2" × .75" | 2.8 | 4 |
| Mixed Fabric | 3" × .75" | 2" × .75" | 3.2 | 4 |
| Edging (ribbed) | 3" 9 mm | 2" × 9 mm | 2.4 | 2.75 |
| Edging (plain) | 3" 9 mm | 2" × 9 mm | 2.25 | 2.5 |

Example Embodiment 4

| Fabric Sample | Size | Stretchable Area | 1 Newton Force Stretch Length (Inches) | 2 Newton Force Stretch Length (Inches) |
|---|---|---|---|---|
| Rib Knit | 3" × .75" | 2" × .75" | 2.75 | 4 |
| Cross Weave | 3" × .75" | 2" × .75" | 3.75 | 5.4 |
| Plain Weave | 3" × .75" | 2" × .75" | 3.5 | 5.25 |
| Mixed Fabric | 3" × .75" | 2" × .75" | 3.5 | 5.25 |
| Edging (ribbed) | 3" 12 mm | 2" × 9 mm | 2.25 | 2.5 |
| Edging (plain) | 3" 12 mm | 2" × 9 mm | 2.25 | 2.75 |

In one aspect of the technology, the material used in connection with the different fabric patterns (e.g., knit, weave, etc.) comprises one or more materials. In one aspect, the material comprises cotton, polyester, spandex, and/or nylon. In one aspect of the technology, the materials comprise anisotropic elastomeric fabric having a relatively low modulus of elasticity intended to provide moderate support for the distended abdomen. The directionality of the stretch of anisotropic fabric is latitudinal, that is from side to side or from the hip to the lumbar region. The modulus of elasticity can vary within relatively broad limits but in one aspect the modulus of elasticity is within the range of at from 3 lb/in$^2$ to about 8 lb/in$^2$. In other aspects of the technology, the fabric is not anisotropic (i.e., it is isotropic), meaning it is intended to stretch vertically, horizontally, and at different angles. In one aspect of the technology, the material used in connection with the main panel 1111 is isotropic. Meaning, it is intended to stretch in latitudinal and non-latitudinal directions. In one aspect of the technology, the modulus of elasticity of the main panel 1111 is at least 1.5 times that material used in connection with the second, third, and fourth materials and can vary within relatively broad limits. In one aspect, the second, third and fourth materials have a modulus of elasticity of at least 4.5 lb/in$^2$ and in one aspect, the modulus varies within a range of from about 6 to 12 lb/in$^2$. In certain aspects of the technology, the fabrics used herein are not exclusively isotropic or anisotropic but have different degrees of stretchability in different directions. For example, the stretchability of the plain weave is substantially similar in all directions while the stretchability of the rib knit is greater in the latitudinal direction than in a longitudinal direction and vice versa. Likewise, in one aspect, the cross weave and mini rib knit have a stretchability that is greater in the latitudinal direction than in a longitudinal direction and vice versa.

In one aspect of the technology, the front piece 1110 comprises connecting edges 1115 disposed about lateral sides of the front piece 1110. The connecting edges 1115 comprise fasteners configured to couple with connecting edges 1220 of back panel 1200.

In one aspect of the technology, a back side of the front piece 1110 (shown, for example, on FIG. 18B) comprises a backing material 1125 disposed about the top 1113 and bottom 1114 corresponding to the placement of the second material 1112 on the front side of the front piece 1110. In one aspect, the backing material 1125 on the back side of front piece 1110 does not circumscribe the main panel 1111 of the front piece 1110. Rather, it is disposed only about the top 1113 and bottom 1114 portions of the front piece correspondence to the location of the second material 1112. In one aspect of the technology, the backing material functions to limit lateral and vertical stretching of the second material 1112 about the top 1113 and bottom 1114 of the front piece 1110 while allowing the second material 1112 about the lateral sides of the main panel 1111 to stretch. In one aspect of the technology, the electric pathways 1103 converge in a central portion 1124 of the main panel 1111 that is expected to correspond to the center top of the maternal abdomen. A covering 1123 is disposed about the central portion 1124 on the back side of the front piece 1110.

Figure 19A:
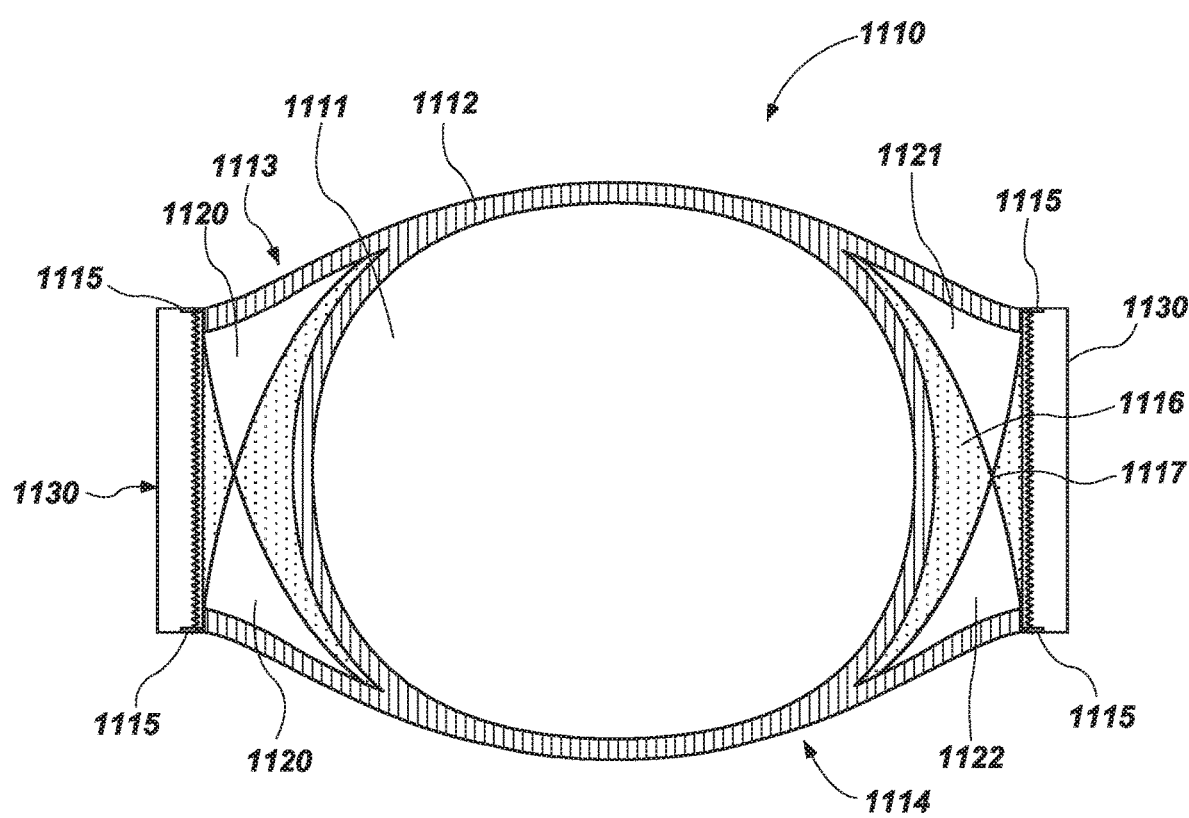
FIG. 19A is a front view of a sensor panel in accordance with one aspect of the technology.
Figure 19B:
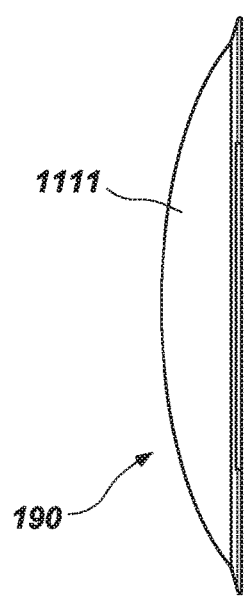
FIG. 19B is a side view of a sensor panel in accordance with one aspect of the technology.
Figure 19C:
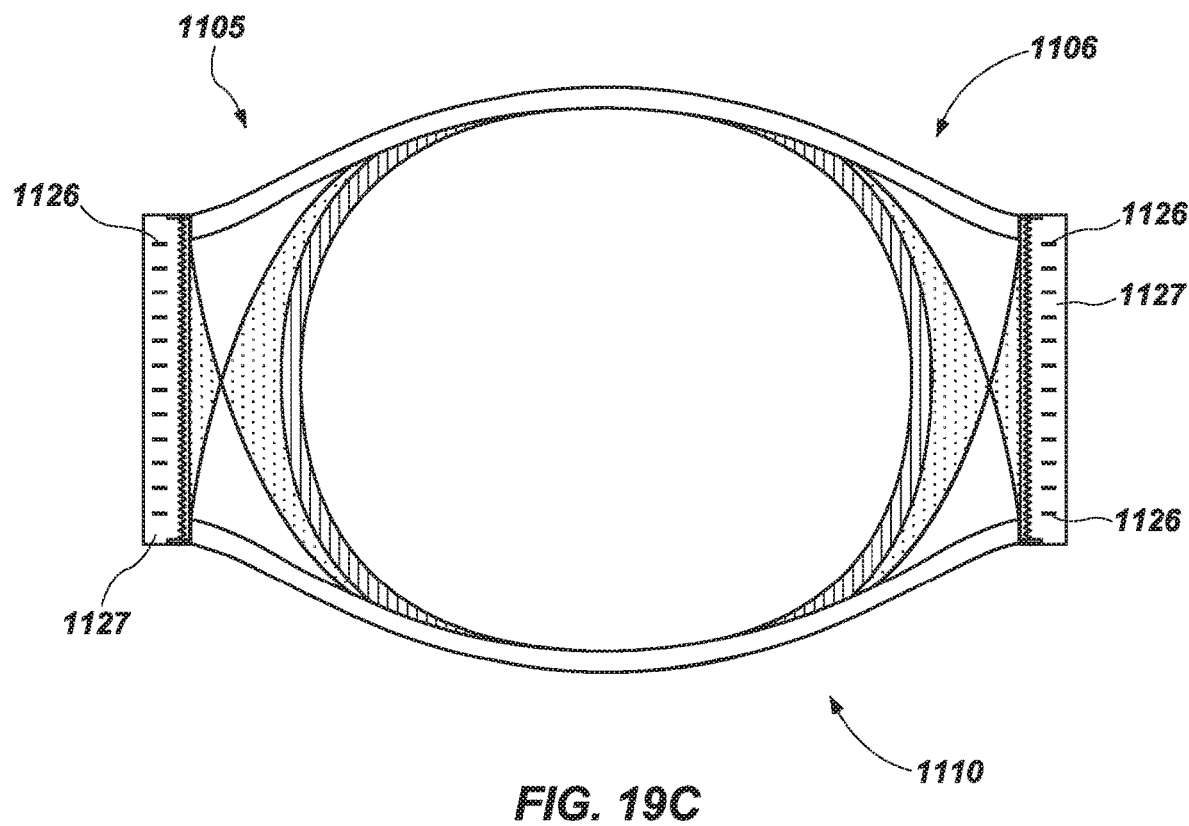
FIG. 19C is a back view of a sensor panel in accordance with one aspect of the technology.
Figure 20A:
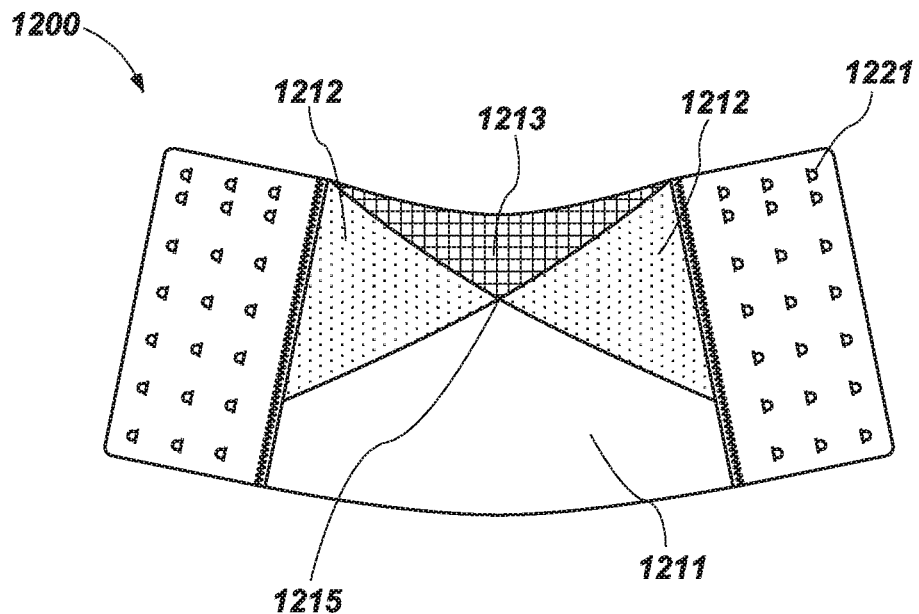
FIG. 20A is a back view of a back panel in accordance with one aspect of the technology.
Figure 20B:
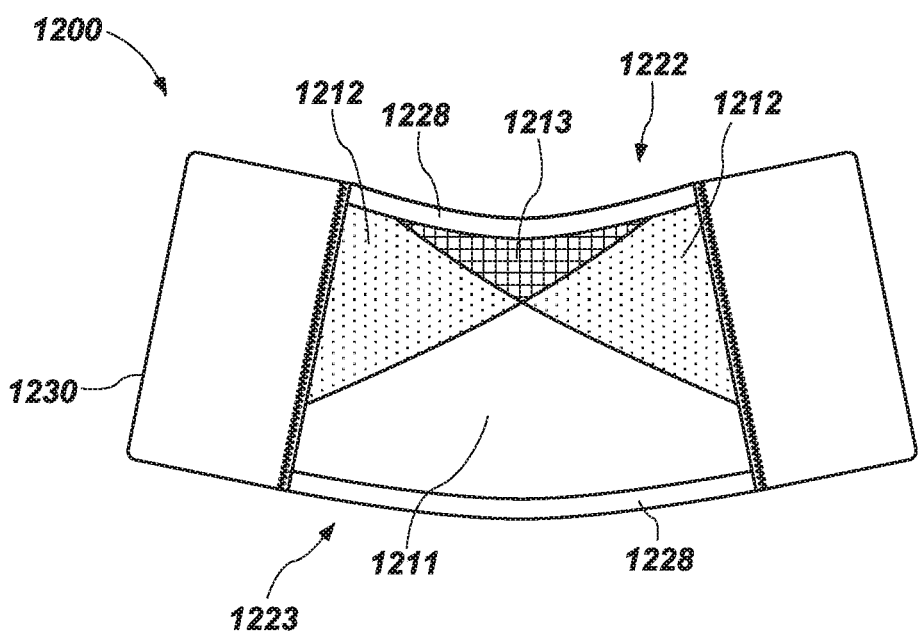
FIG. 20B is a front view of a back panel in accordance with one aspect of the technology.
Figure 21A:
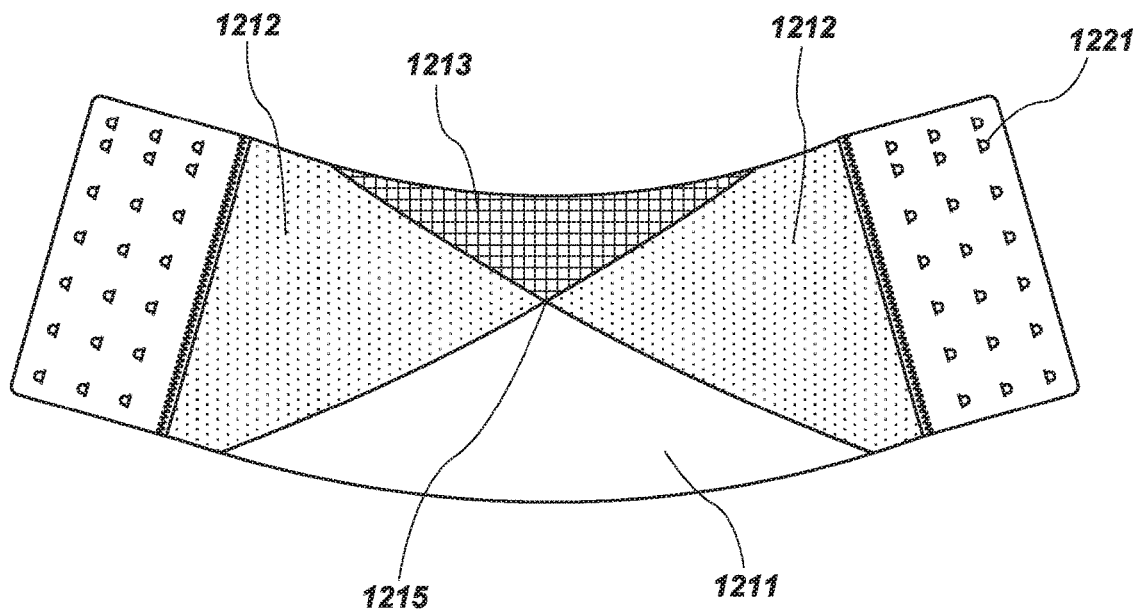
FIG. 21A is a back view of a back panel in accordance with one aspect of the technology.
Figure 21B:
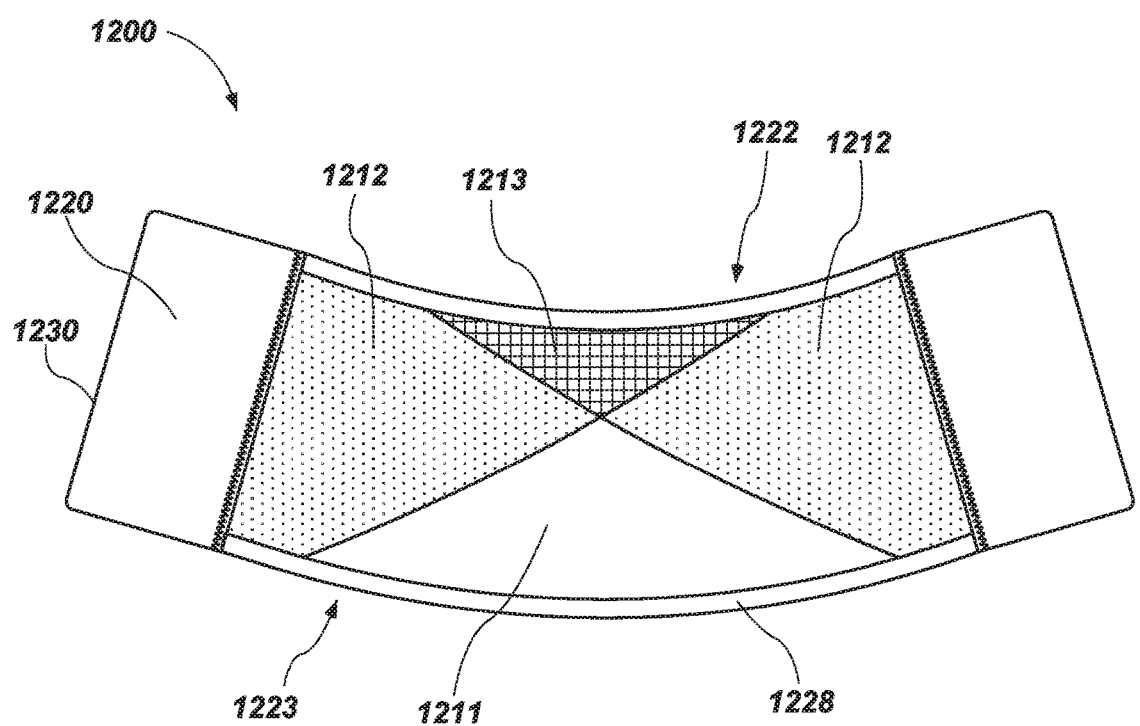
FIG. 21B is a front view of a back panel in accordance with one aspect of the technology.
Figure 22A:
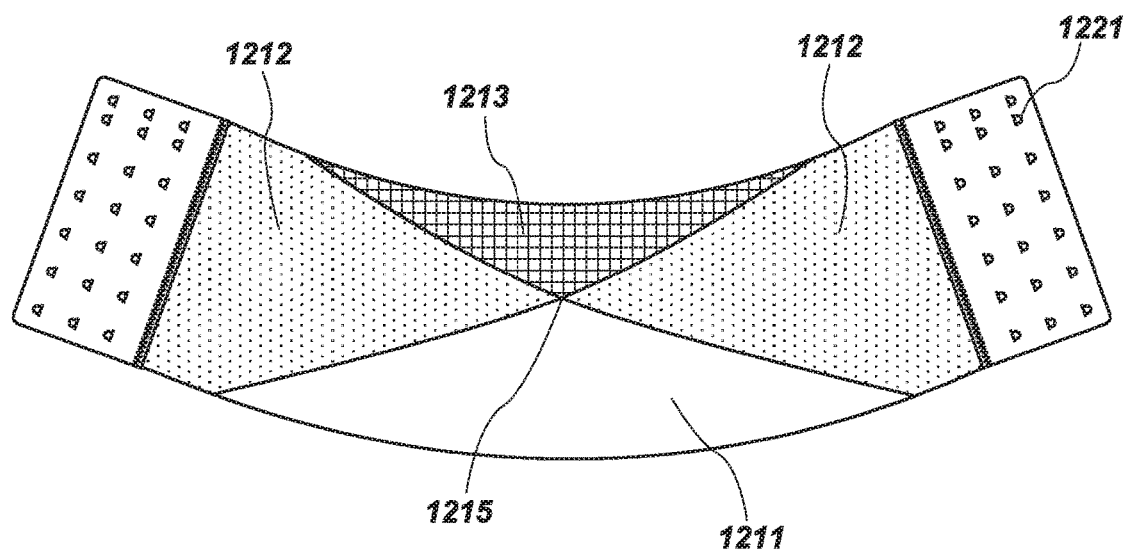
FIG. 22A is a back view of a back panel in accordance with one aspect of the technology.
Figure 22B:
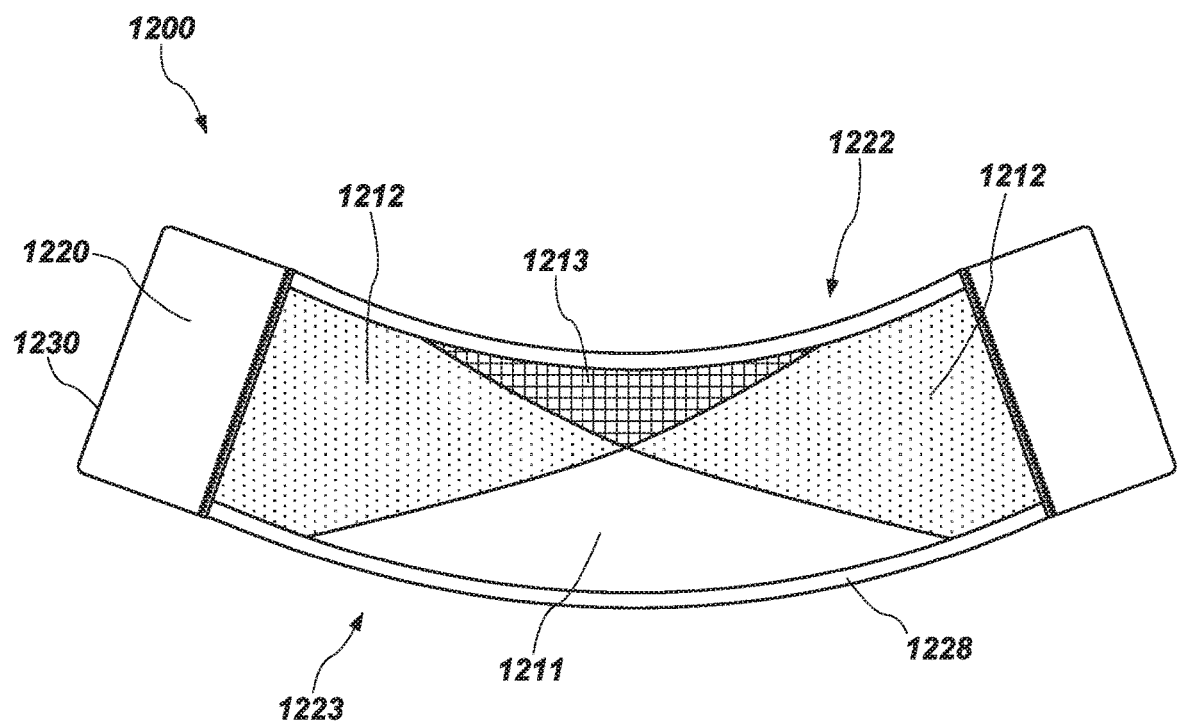
FIG. 22B is a front view of a back panel in accordance with one aspect of the technology.
Figure 23:
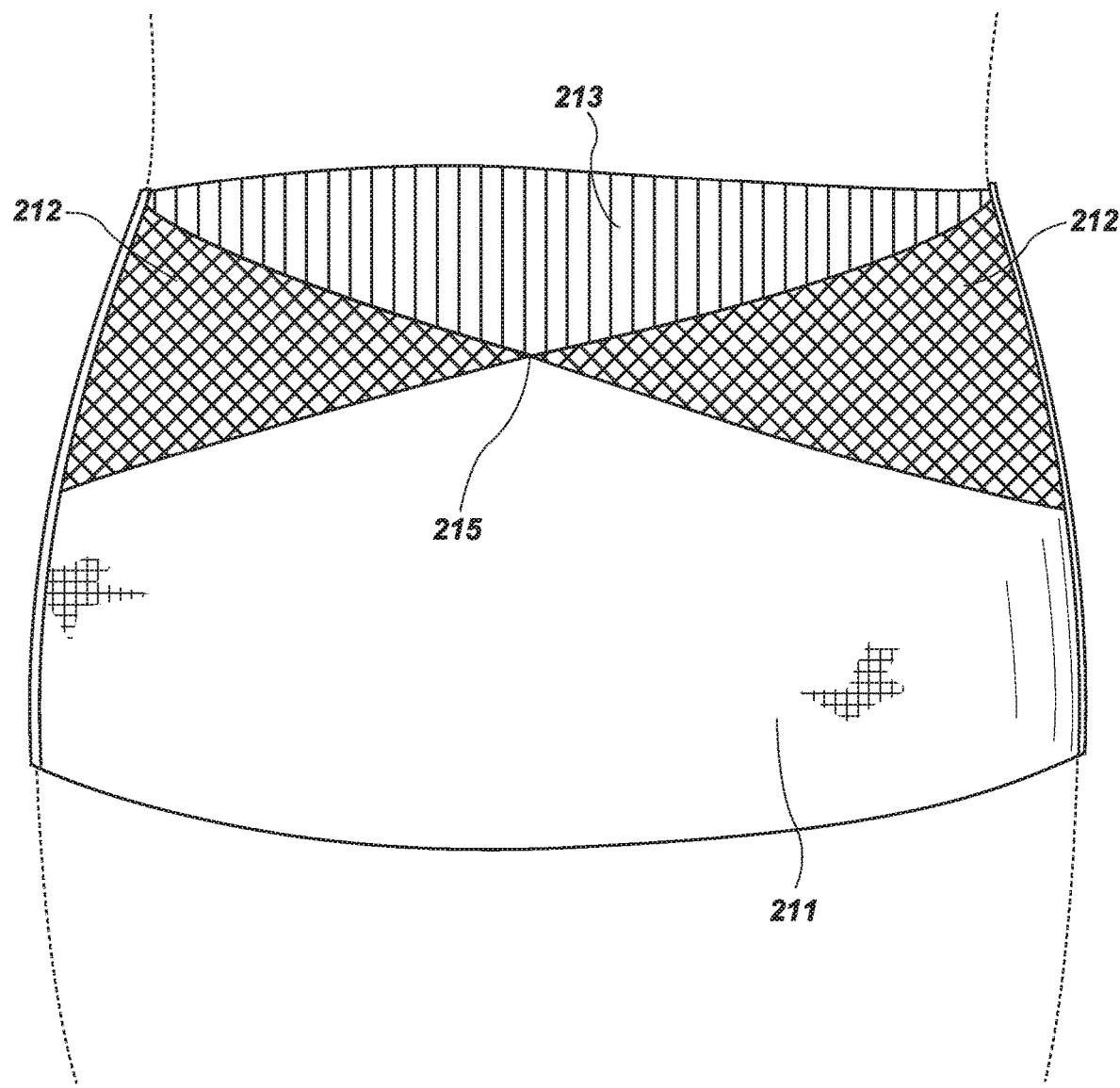
FIG. 23 is a front view of a back panel on the waist of a user in accordance with one aspect of the technology.
Figure 24:
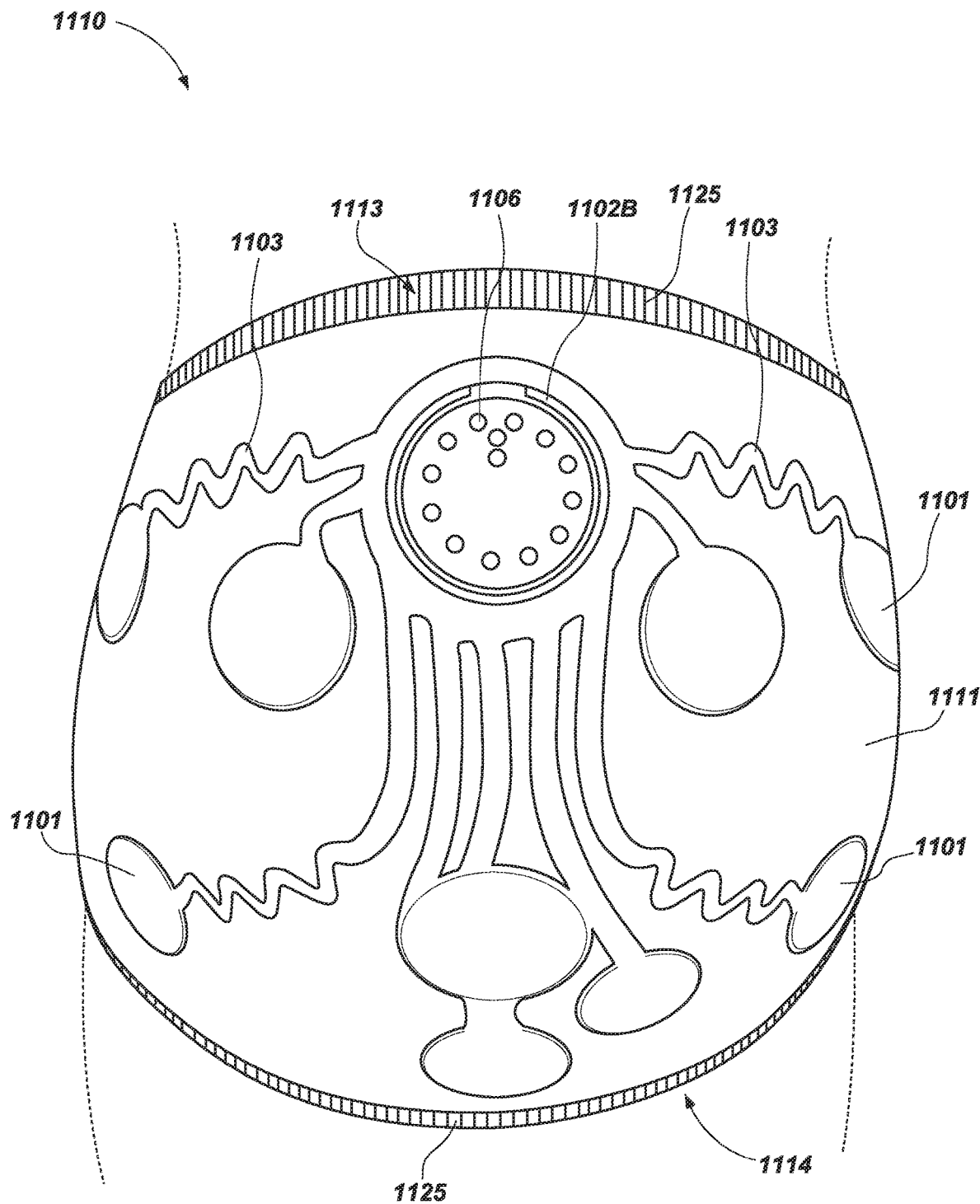
FIG. 24 is a front view of a sensor panel on the abdomen of a user in accordance with one aspect of the technology.
Figure 25:
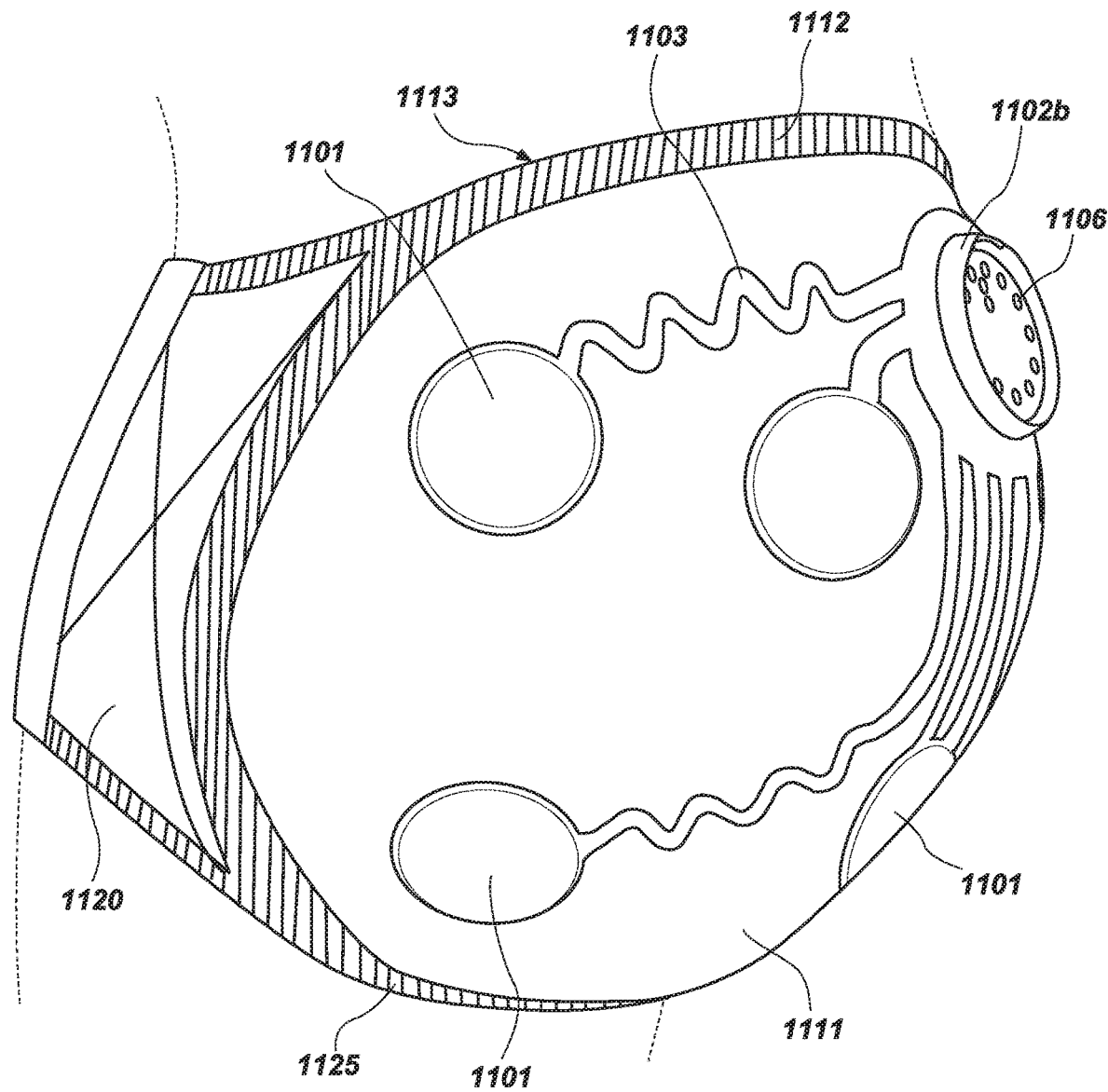
FIG. 25 is a side view of a sensor panel on the abdomen of a user in accordance with one aspect of the technology.
Figure 26:
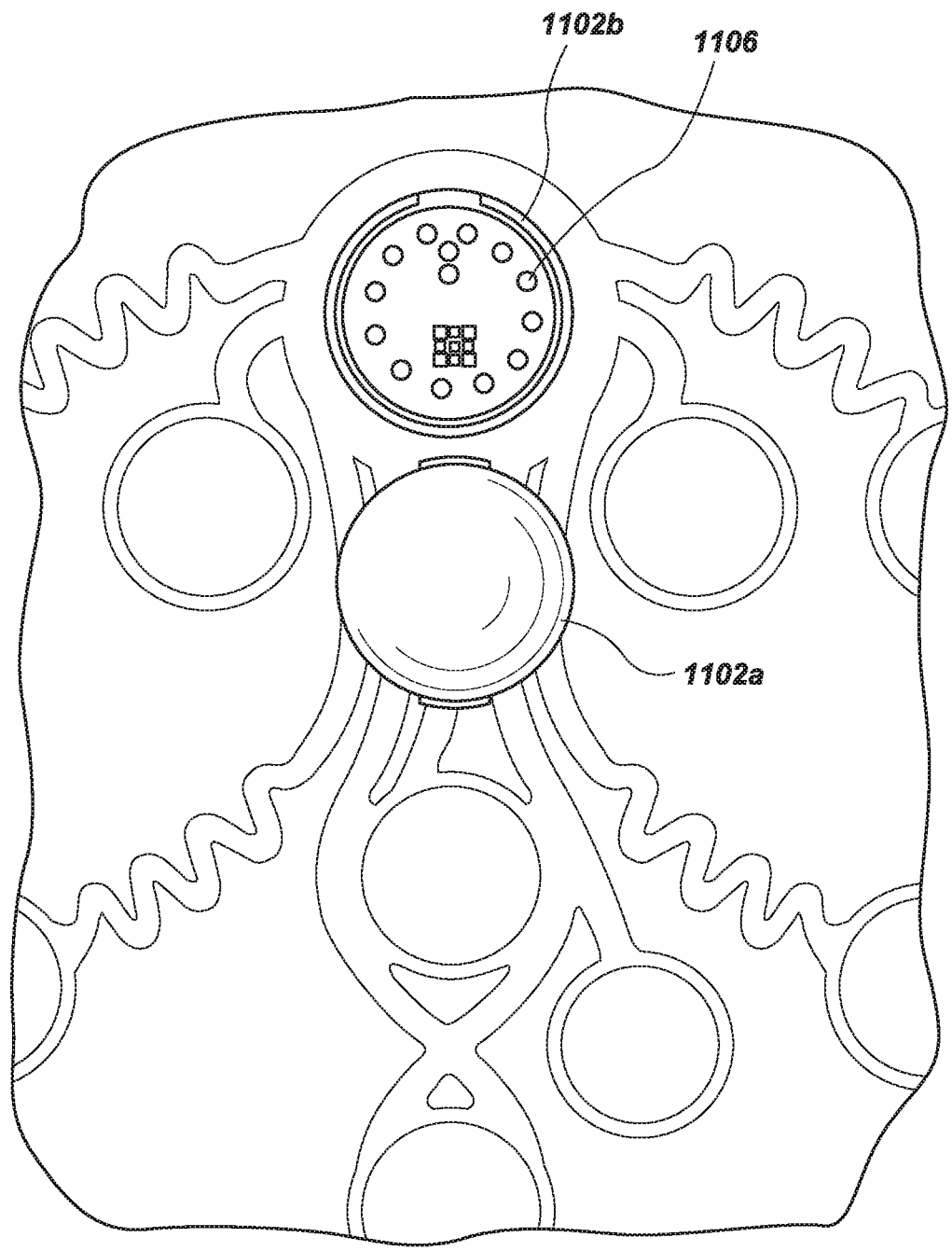
FIG. 26 is a front view of a portion of a sensor panel in accordance with one aspect of the technology with a cover of the monitor controller removed.
Figure 27:
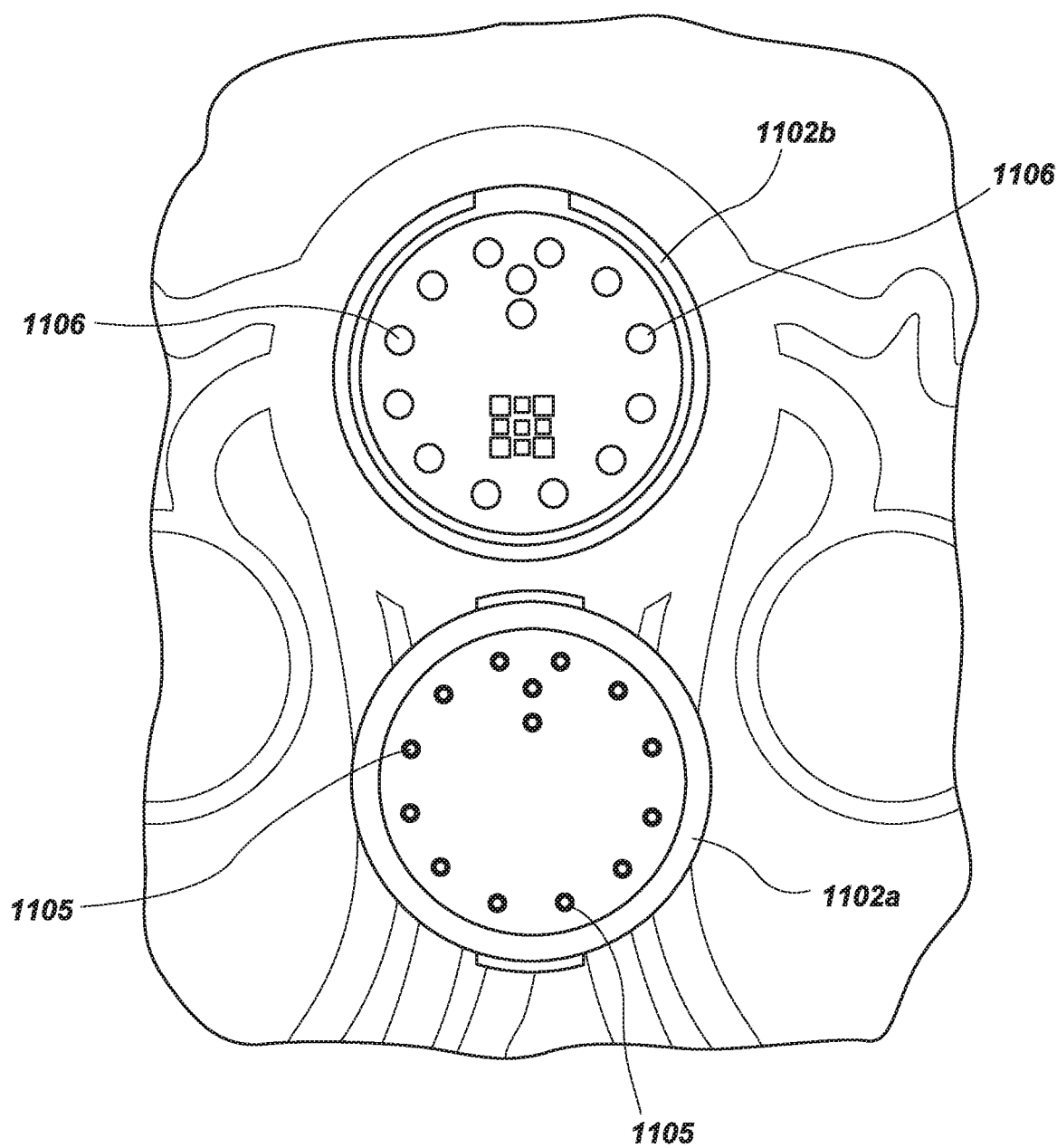
FIG. 27 is a front view of a portion of a sensor panel in accordance with one aspect of the technology showing a bottom portion of the cover of the monitor controller.

In accordance with one aspect of the technology, the back piece or back panel 1200 of the device comprises a central panel 1205 with connecting edges 1220 disposed about lateral sides of the central panel 1205. Each of the connecting edges 1220 comprises a plurality of fasteners configured to mate with fasteners disposed about connecting edges. In one aspect of the technology, the fasteners comprise a hook and loop configuration, as shown in FIGS. 19C and 22A. For example, in one aspect of the technology, a back side of the connecting edge 1220 of the back panel 1200 comprises a plurality of loops 1221. The loops 1221 are configured to couple with hooks 1126 disposed about connecting edges 1115 of the front piece 1110. In one aspect of the technology, fasteners (e.g., hooks, loops, snaps, or other fasteners) are coupled to a semi-rigid interface 1127 comprising, in one aspect, a flexible or stretchable polymer. The interface 1127 is coupled to a piece of fabric comprising slits or openings that correspond to the location of the fasteners disposed about the interface 1127. As the interface 1127 is coupled to the fabric, the fasteners are pushed through the openings in the fabric. In one aspect of the technology, the fabric is shaped to be about twice the size of the interface 1127 so that the interface 1127 can be disposed about a first half of the fabric while a second half of the fabric is folded about a back side of the interface 1127.

In one aspect of the technology, the central panel of back panel 1200 comprises a plurality of fabrics configured to support the front piece 1110 about the expectant mother to maximize contact between the electrodes 1101 and the maternal abdomen while also supporting the back of the expectant mother and providing for pivoting movement. In one aspect of the technology, the central panel 1205 comprises a first material disposed about a bottom portion 1211 that tapers to a pivoting point 1215 about a center portion of the central panel 1205 and back panel 1200. Side portions 1212 comprising a second material extend from lateral sides of the central panel above the bottom portion 1211 to the pivot point 1215 forming a generally triangular shape fit between the bottom portion 1211 and a top portion 1213. In one aspect, the top portion 1213 comprises a third material. As with the front piece 1110, the different materials of the back panel 1200 are configured to optimize stretching. In one aspect of the technology, the first material (e.g., the material used with the bottom portion 1211) is the most stretchable out of the three materials. The top portion 1213 is the second most stretchable and the side portions 1212 are the third most stretchable. In one aspect of the technology, the bottom portion 1211 comprises a plain weave, the top portion 1213 comprises a rib knit, and the side portions 1212 comprise a cross-weave. As with the front piece 1110, it is understood that different combinations of materials and different shaped portions of the back panel 1200 are contemplated herein without departing from the spirit of the technology. For example, the top portion 1213 and side portions 1212 may comprise the same material in certain aspects. In other aspects, the top portion 1213 and bottom portion 1211 may comprise the same material. In addition, the different portions 1211, 1212, 1213 may be more curvilinear at the interface between different portions, rather than linear, so long as at least two portions comprise materials of different stretchability that converge at a center point or pivot point 1215. The pivot point 1215 is configured to correspond to a center portion of the back of the expectant mother.

In one aspect of the technology, the central panel 1205 and connecting edges 1220 are configured together to comprise a substantially linear outer edge 1230 and curvilinear top 1222 and bottom 1223. The linear outer edge 1230 is configured to facilitate coupling to the connecting edge 1115 of the front piece 1110 and may comprise a plurality of different configurations. The curvilinear top 1221 and bottom 1223 of the back panel 1200 are curved in the same direction and are configured to maximize the comfort of the expectant mother. In one aspect of the technology, the radius of curvature of the curvilinear top 1221 and bottom 1222 of the back panel decreases depending on the overall size of the back panel 1200. In one aspect, the radius of curvature of the back panel 1200 ranges from about 200 mm to 500 mm, the larger back panel having the larger radius of curvature. In one aspect, a back side (or the side intended to contact the back of the mother) comprises an edging 1228 disposed about a top edge and bottom edge of the back panel 1200.

The foregoing detailed description describes the technology with reference to specific exemplary embodiments. However, it will be appreciated that various modifications and changes can be made without departing from the scope of the present disclosure as set forth in the appended claims. The detailed description and accompanying drawings are to be regarded as merely illustrative, rather than as restrictive, and all such modifications or changes, if any, are intended to fall within the scope of the present disclosure as described and set forth herein.

More specifically, while illustrative exemplary invention embodiments have been described herein, the disclosure is not limited to these embodiments, but includes any and all embodiments having modifications, omissions, combinations (e.g., of aspects across various embodiments), adaptations and/or alterations as would be appreciated by those skilled in the art based on the foregoing detailed description. The limitations in any claims are to be interpreted broadly based on the language employed in the claims and not limited to examples described in the foregoing detailed description or during the prosecution of the application, which examples are to be construed as non-exclusive. For example, in the present disclosure, the term "preferably" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the disclosure should be determined solely by the appended claims and their legal equivalents, rather than by the descriptions and examples given above.

The invention claimed is:

1. A method of manufacturing a garment shaped to approximate the abdomen of a pregnant female human having a layered laminated conductive material forming a circuit assembly adhered to the garment, comprising:
    disposing a stretchable first conductive layer comprising silver on a stretchable substrate forming a plurality of sensors and conductive traces, wherein the conductive traces connect each of the plurality of sensors to one or more conductive leads;
    disposing a second stretchable conductive layer comprising a carbon composite atop the first conductive layer, wherein the second conductive layer is shaped to approximate the first conductive layer;
    disposing an encapsulating layer about the conductive traces and about a perimeter of the sensors leaving a face of the sensors exposed; and
    disposing the substrate on the garment wherein the exposed face of the sensors remains exposed.

2. The method of claim 1, further comprising disposing a third conductive layer atop the second stretchable conductive layer.

3. The method of claim 1, further comprising disposing a monitor controller about the garment coupled to each of the conductive leads, wherein the monitor controller comprises a control unit configured to receive electrical signals from the sensors and transmit information related to the electrical signals to a remote location.

4. The method of claim 1, wherein the garment comprises a concave front panel coupled to a substantially planar back panel.

5. The method of claim 4, wherein the substrate is disposed about the concave front panel of the garment.

6. The method of claim 1, wherein the garment comprises a first set of sensors selected from the plurality of sensors disposed about a top portion of the garment and a second set of sensors selected from the plurality of sensors disposed about a bottom portion of the garment, said first set of sensors and said second set of sensors being disposed symmetrically about an imaginary axis extending through a center of the garment parallel to a longitudinal axis of a front panel of the garment.

7. A method of manufacturing a garment shaped to approximate the abdomen of a pregnant female human having a layered laminated conductive material forming a circuit assembly adhered to the garment, comprising:
    disposing a stretchable first conductive layer comprising silver on a stretchable substrate forming a plurality of sensors and conductive traces, wherein the conductive traces connect each of the plurality of sensors to one or more conductive leads;
    disposing a second stretchable conductive layer comprising a carbon composite atop the first conductive layer, wherein the second conductive layer is shaped to approximate the first conductive layer;
    disposing an encapsulating layer about the conductive traces and about a perimeter of the sensors leaving a face of the sensors exposed;
    disposing the substrate on the garment wherein the exposed face of the sensors remain exposed; and
    disposing a thermoplastic layer about the substrate, the thermoplastic layer comprising a graphic print layer sized to approximate the shape of the first conductive layer.

8. The method of claim 7, further comprising cutting the thermoplastic layer to approximate the shape of the first conductive layer.

9. The method of claim 7, further comprising the step of cutting the substrate to approximate the shape of the second conductive layer after the thermoplastic layer is disposed about the substrate.

* * * * *